United States Patent
Amirouche et al.

(10) Patent No.: US 9,523,358 B2
(45) Date of Patent: Dec. 20, 2016

(54) MAGNETICALLY DRIVEN MICROPUMP

(75) Inventors: Farid Amirouche, Chicago, IL (US); Yu Zhou, Chicago, IL (US); Matthew Lawrence Cantwell, Chicago, IL (US); Johan Citerin, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 1248 days.

(21) Appl. No.: 13/145,831

(22) PCT Filed: Sep. 30, 2009

(86) PCT No.: PCT/US2009/059020
§ 371 (c)(1),
(2), (4) Date: Jul. 22, 2011

(87) PCT Pub. No.: WO2010/093383
PCT Pub. Date: Aug. 19, 2010

(65) Prior Publication Data
US 2011/0274566 A1    Nov. 10, 2011

Related U.S. Application Data

(60) Provisional application No. 61/152,165, filed on Feb. 12, 2009.

(51) Int. Cl.
*F04B 43/02*    (2006.01)
*F04B 43/04*    (2006.01)
(Continued)

(52) U.S. Cl.
CPC ........ *F04B 43/043* (2013.01); *A61M 5/14224* (2013.01); *F04B 43/02* (2013.01);
(Continued)

(58) Field of Classification Search
CPC ....... F04B 43/02; F04B 43/021; F04B 43/023; F04B 43/025; F04B 43/026; F04B 43/04; F04B 43/043; F04B 43/028; Y10T 29/49236; F16K 99/0001; F16K 99/0015; F16K 99/046; A61M 5/1422; A61M 5/14224; A61M 2205/0244
(Continued)

(56) References Cited

U.S. PATENT DOCUMENTS 4,743,169 A  *  5/1988  Funakawa et al. ........... 417/306
4,786,240 A  *  11/1988  Koroly et al. ............. 417/413.1
(Continued)

FOREIGN PATENT DOCUMENTS

DE    19548949 A1  *  7/1997
GB    2248891         4/1992
(Continued)

OTHER PUBLICATIONS

Khoo, Melvin, et al. "Micro magnetic silicone elastomer membrane actuator", 2000.*
(Continued)

*Primary Examiner* — Alexander Comley
*Assistant Examiner* — Nathan Zollinger
(74) *Attorney, Agent, or Firm* — McDonnell Boehnen Hulbert & Berghoff LLP

(57) ABSTRACT

A magnetically driven micropump for handling small fluid volumes. The micropump includes a first chamber and a second chamber. A flexible membrane being disposed between the first and second chambers. The flexible membrane being magnetically coupled to an actuator for displacing the membrane.

41 Claims, 30 Drawing Sheets

(51) Int. Cl.
*F16K 99/00* (2006.01)
*A61M 5/142* (2006.01)

(52) U.S. Cl.
CPC ........ *F04B 43/028* (2013.01); *F16K 99/0001* (2013.01); *F16K 99/0015* (2013.01); *F16K 99/0046* (2013.01); *A61M 5/1422* (2013.01); *A61M 2205/0244* (2013.01)

(58) Field of Classification Search
USPC .... 417/322, 413.1, 420; 29/888.02; 249/155
See application file for complete search history.

(56) References Cited

U.S. PATENT DOCUMENTS

| | | | | |
|---|---|---|---|---|
| 4,790,937 | A | * | 12/1988 | Eilers ................ A61M 1/16 210/321.71 |
| 5,011,380 | A | * | 4/1991 | Kovacs ........................ 417/413.1 |
| 5,338,164 | A | * | 8/1994 | Sutton et al. ............... 417/413.2 |
| 5,413,599 | A | * | 5/1995 | Imachi et al. ................ 623/1.24 |
| 8,308,452 | B2 | * | 11/2012 | Amirouche et al. ....... 417/413.2 |
| 8,807,965 | B2 | * | 8/2014 | Stenberg ............. F04B 43/0081 417/413.1 |
| 2003/0180164 | A1 | | 9/2003 | Bunner et al. |
| 2005/0069424 | A1 | * | 3/2005 | Lu et al. ........................... 417/322 |
| 2005/0219288 | A1 | * | 10/2005 | Vogeley et al. ................. 347/10 |
| 2007/0205853 | A1 | * | 9/2007 | Taya et al. ..................... 335/205 |
| 2012/0083759 | A1 | * | 4/2012 | Kirkpatrick ............ F04B 43/04 604/500 |

FOREIGN PATENT DOCUMENTS

| | | | |
|---|---|---|---|
| JP | 03149374 | A * | 6/1991 |
| JP | 05231327 | A * | 9/1993 |
| JP | H05-231327 | | 9/1993 |
| JP | 07279850 | A * | 10/1995 |
| JP | 2008-240663 | | 10/2008 |
| WO | 2004/067964 | | 8/2004 |
| WO | 2006/111775 | | 10/2006 |

OTHER PUBLICATIONS

English Abstract for DE19548949A1 dated Jul. 1997.*
International Search Report for Int. Patent App. No. PCT/US2009/059020, mailed Mar. 9, 2010.
Rapp R et al: "Liga Micropump for Gases and Liquids" Sensors and Actuators A, Elsevier Sequoia S.A., Lausanne, CH, vol. A40, No. 1, Jan. 1, 1994 (Jan. 1, 1994), pp. 57-61, XP000434539 ISSN: 0924-4247.
Japanese Office Action for JP App. No. 2011-550111, mailed Sep. 2, 2014.

* cited by examiner

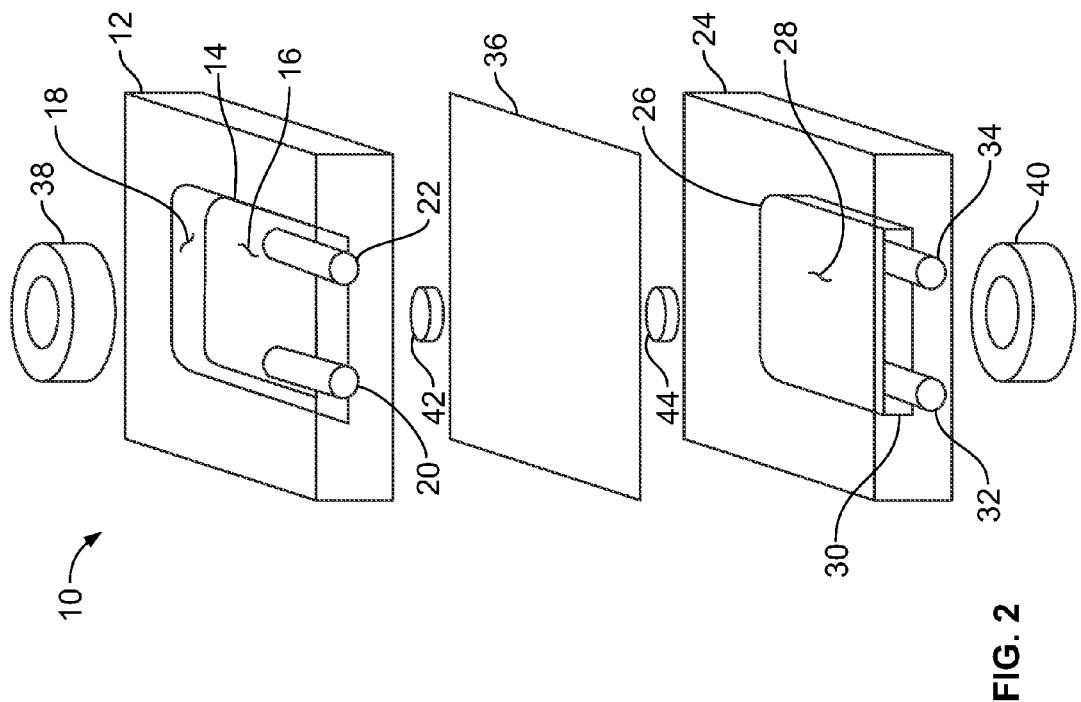
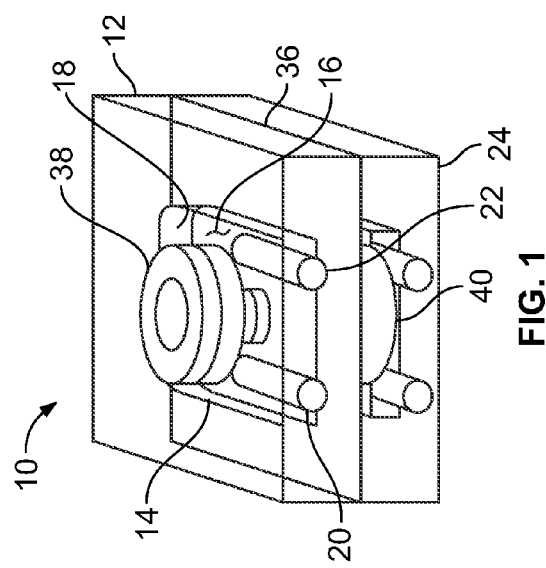
FIG. 1
FIG. 2

Magnetic field intensity at the sensor level after a pulse of short duration

Electric current flowing in the coils after a pulse of short duration

Contribution of the coils to the magnetic field intensity at the sensor level as a function of current

MAGNETICALLY DRIVEN MICROPUMP

CROSS REFERENCE TO RELATED APPLICATIONS

The present application is a U.S. National Phase Application pursuant to 35 U.S.C. §371 of International Application No. PCT/US2009/059020 filed Sep. 30, 2009, which claims priority to U.S. provisional patent application Ser. No. 61/152,165 filed on Feb. 12, 2009. The entire disclosure contents of these applications are herewith incorporated by reference into the present application.

BACKGROUND

The present disclosure relates to a magnetically driven micropump for handling small fluid volumes. In particular, the present disclosure related to a micropump including a magnetically actuated membrane to transfer fluids.

The field of microfluidics generally encompasses handling very small fluid volumes on the order of several nanoliters. Microfluidics has increasingly important applications in such fields as life sciences and chemical analysis. Microfluidics devices, also known as micromechanical systems (MEMS), include devices for fluid control, fluid measurement, medical testing, DNA and protein analysis, in vivo drug delivery, and other biomedical applications.

Typical fluid flow rates of micropumps range from approximately 0.1 microliter per minute to several (80-180) milliters per minute. Flow rates on this order are useful in applications such as disposable micro total analysis systems (µTAS) or lab-on-a-chip (LOC) for chemical and biological analysis, point of care testing (POCT) for medical diagnostic testing, implantable drug delivery systems for medications (such as insulin) requiring a fine degree of regulation and precise control, and cardiology systems for blood transport and pressurization.

Since most of MEMS processing techniques evolved from microelectronics, the first silicon micropump was based on a piezoelectric actuation of a thin membrane in 1980s primarily for use in the controlled insulin delivery systems. This work demonstrated the feasibility of silicon-based micropump and inspired extensive research on silicon micropumps. Also, several commercially available implantable silicon micropumps were reported for insulin delivery and therapeutic agents dispensing through pharmaceutical and clinical therapy fields.

Recently, a number of polymeric materials and new microfabrication techniques, such as soft lithography, microstereolithography, micromolding and polymeric surface micromachining, have been investigated and developed for a growing trend of low cost, integrated and miniaturized disposable µTAS applications. Many polymeric materials including plastics and elastomers have been increasingly incorporated into other microdevices as substrates, structural membranes, and functional membranes due to their excellent mechanical properties, good chemical resistance, and low fabrication cost. Among the most popular polymers, polydimethylsiloxane (PDMS) has been extensively utilized in microfluidic devices because of excellent biocompatibility, simple fabrication process (molding and reversible bonding) and optical transparency (facilitating monitoring and interrogating) as well as elasticity (good sealing and connecting).

Silicon-based and plastic-based valveless micropumps are taken as an example to compare with polymer-based micropump. The fabrication process of the silicon-based micropump involved three subsequent Deep Reactive Ion Etching (DRIE) steps and one silicon-glass anodic bonding step while LIGA, microinjection, or hot embossing molding and multiple thin plate assembly with adhesives or bolts was involved for the plastic pumps. On the other hand, for a PDMS-based micropump only multilayer soft lithography processes and PDMS-PDMS bonding techniques are required. From the fabrication cost point of view, a PDMS-based micropump is considerably lower than the former two types of micropumps.

Furthermore, the main challenge of the plastic micropump is the high fluid leakage due to the surface roughness of the thin plastic layers. Bolt-assembly makes matters even worse because the stress is concentrated on the interface between the layers where bolts were connected. The adhesive bonding also tends to contribute to blockage of the microstructures. Therefore, the PDMS is a practical (short process time and low cost) material for micropumps.

SUMMARY

The micropump disclosed herein is operated according to the principle that an oscillating membrane results in a variation of pressure in the chamber, which directs the dynamic flow of the fluidic conduit by the form of passive valves. Often passive valves are incorporated as check valves in inlets and outlets of reciprocating micropumps in the forms of cantilever flaps, bridge membranes, spherical balls, mobile structures, nozzles/diffusers or Tesla elements. However, a valveless micropump integrating nozzle/diffuser elements are of particular interest for disposable µTAS applications, such as in biomedicine and biochemistry, since the risk of suspended particles clogging, wearing and fatiguing moving mechanical components can be reduced and practically eliminated. Moreover, the simple realization and planar feature of nozzles/diffusers make low cost and miniaturization of the micropump for disposable applications possible.

The valveless micropump of the present disclosure consists of a nozzle and diffuser element, a fluid chamber and an oscillating actuation membrane. The membrane is integrated with small bulk magnets takes advantage of large attractive or repulsive magnetic forces and membrane deflection. The alternating perpendicular magnetic forces on the membrane result in a large volumetric stroke, which is desired for a high flow rate micropump. In addition, magnetic actuation is an externally applied field where the micropump is controlled by an air gap. Thus, the electric connectors for applied current or voltage on the micropump can be avoided, which also provides a potential for miniaturization as in the µTAS applications.

The principles and operation of the subject matter of the present disclosure are fully explained in Zhou et al., *Fluid Damping Effects on Resonant Frequency of an Electromagnetically-Actuated Valveless Micropump*, International Journal of Advanced Manufacturing Technology, Apr. 24, 2009, which is herein incorporated by reference in its entirety.

An aspect of the present disclosure includes a micropump for delivering a fluid. The micropump includes a pump assembly having a first pump body defining a first fluid body flow path. The first pump body includes a first chamber, the first chamber including a first chamber wall and a first side wall, a first inlet and a first outlet, wherein the first inlet and first outlet are in fluid communication with the first chamber. The pump assembly also includes a second pump body defining a second fluid body flow path. The second pump body includes a second chamber, the second chamber including a second chamber wall and a second side wall, a second inlet and a second outlet, wherein the second inlet and the second outlet are in fluid communication with the second chamber. The pump assembly also includes a flexible membrane disposed between the first chamber and the second chamber. The micropump also including an actuator assembly configured to cooperate with the pump assembly. The actuator assembly includes a driver magnetically coupled to the membrane, and a sensor configured to detect the position of the membrane, wherein the driver applies a magnetic force to the membrane, causing the membrane to deflect, and wherein such deflection of the membrane results in a change of pressure within the first chamber and the second chamber thereby resulting in fluid flow.

Another aspect of the present disclosure includes a micropump assembly for delivering a fluid from a fluid reservoir, the micropump assembly including a pump cartridge. The pump cartridge includes a first pump body defining a first chamber, the first chamber including a first chamber wall and a first side wall, a first inlet and a first outlet, wherein the first inlet and first outlet are in fluid communication with the first chamber. The pump cartridge further including a second pump housing defining a second chamber, the second chamber including a second chamber wall and a second side wall, a second inlet and a second outlet, wherein the second inlet and the second outlet are in fluid communication with the second chamber, and a flexible membrane disposed between the first chamber and the second chamber, wherein the pump cartridge is configured to allow fluid communication from the fluid reservoir to at least one of the first chamber and the second chamber. The micropump assembly further including a housing enclosing an actuator assembly configured to cooperate with the micropump cartridge. The actuator assembly includes a driver magnetically coupled to the membrane, and a first sensor configured to detect the position of the membrane, wherein the driver applies a magnetic force to the membrane, causing the membrane to deflect, and wherein such deflection of the membrane results in a change of pressure within the first chamber and the second chamber thereby resulting in fluid flow. The micropump assembly further including a controller coupled to the driver and configured to control the position of the membrane by receiving input from the first sensor and adjusting the magnetic force applied by the driver. The micropump assembly further including a power supply configured to energize the driver and the controller, wherein the housing is configured such that the micropump cartridge may be inserted into and retained within the actuator assembly.

Another aspect of the present disclosure is a method of fabricating a micropump. The method includes the steps of: fabricating a flexible membrane from a polymer material including the steps of spin coating a first polymer layer on a silicon wafer and allowing the first polymer layer to cure, placing magnetic material on the first polymer layer, applying a second polymer layer around the magnetic material and allowing the second polymer layer to cure, and applying a third polymer layer and allowing the third polymer layer to cure; fabricating a rigid pump body by pouring liquid polymer material into a mold configured to form a fluid chamber, an inlet channel, and an outlet channel, and allowing the liquid polymer to cure; aligning the flexible membrane with the rigid pump body; and bonding the flexible polymer membrane to the rigid pump body.

Another aspect of the present disclosure is a micropump for delivering a fluid. The micropump includes a pump assembly having a first pump body defining a first chamber. The first chamber includes a first chamber wall and a first side wall, a first inlet and a first outlet, wherein the first inlet and first outlet are in fluid communication with the first chamber, and a first flexible membrane disposed over the first chamber opposite the first chamber wall. The pump assembly having a second pump body defining a second chamber, the second chamber including a second chamber wall and a second side wall, a second inlet and a second outlet, wherein the second inlet and the second outlet are in fluid communication with the second chamber, and a second flexible membrane disposed over the second chamber opposite the second chamber wall. The pump assembly further includes at least a third pump body disposed between the first pump body and the second pump body. The third pump body defining a third chamber including a third side wall, third inlet and a third outlet, wherein the third inlet and the third outlet are in fluid communication with the third chamber, wherein the at least third chamber is adjacent the first membrane and the second membrane. The micropump assembly further includes an actuator assembly configured to cooperate with the pump assembly. The actuator assembly includes a driver magnetically coupled to the first membrane and the second membrane, and at least one sensor configured to detect the position of the first membrane and the second membrane, wherein the driver applies a magnetic force to the first membrane and the second membrane, causing the first membrane and the second membrane to deflect, and wherein such deflection of the first membrane and the second membrane results in a change of pressure within the first chamber, the second chamber, and the third chamber thereby resulting in fluid flow.

BRIEF DESCRIPTION OF THE DRAWINGS

The present disclosure will be described hereafter with reference to the attached drawings which are given as a non-limiting example only, in which:

FIG. 1 is a perspective view of an embodiment of the micropump assembly of the present disclosure;

FIG. 2 is an exploded view of the micropump assembly of FIG. 1;

DETAILED DESCRIPTION

Figure 3:
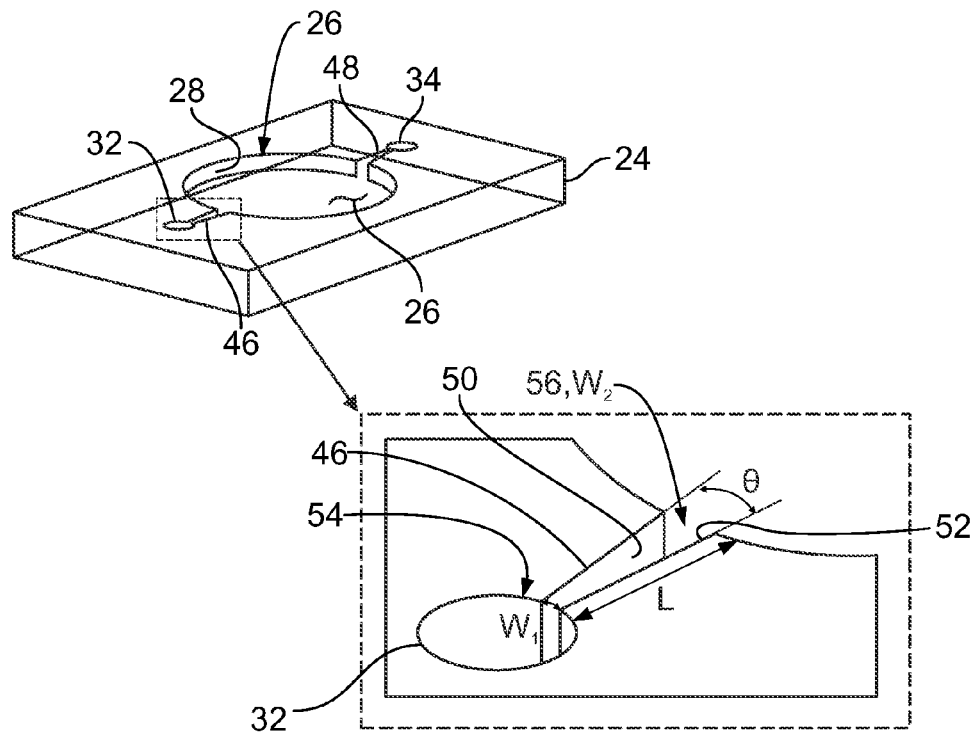
FIG. 3 is a perspective view of a pump body having nozzle/diffuser flow elements to produce unidirectional flow.

Referring now to FIGS. 1 and 2, the micropump of the present disclosure includes a pump assembly 10 having a first pump body 12 and a second pump body 24 and a flexible membrane 36 disposed therebetween. The first pump body 12 defines a first body flow path and includes a first chamber 14 having a first chamber wall 16 and a first sidewall 18. The first pump body 12 further includes a first inlet 20 and a first outlet 22 in fluid communication with the first chamber 14. Likewise, the second pump body 24 defines a second body flow path and includes a second chamber 26 having a second chamber wall 28 and a second sidewall 30. The second pump body 24 further includes a second inlet 32 and a second outlet 34 in fluid communication with the second chamber 26.

The micropump of the present disclosure also includes a driver magnetically coupled to the flexible membrane 36. In the embodiment shown in FIGS. 1 and 2, the driver includes a first magnetic coil 38 and a second magnetic coil 40. The magnetic coils 38, 40 are configured to impart a magnetic force upon the flexible membrane 36 through electromagnetic coupling with magnets 42, 44.

The micropump of the present disclosure is intended to impart unidirectional flow to a fluid. Such unidirectional flow may be achieved with or without check valves. The typical operation flow rate of a micropump is approximately in the range of a few microliters to milliliters per minute (for a non-mechanical micropump is less than 10 μl/min while for a mechanical micropump the average flow rate is up to several milliliters). Thus, a broad range of biomedical applications are found in applications such as the fluid fine regulation and precise control systems for implantable drug delivery, chemical and biological detection, as well as blood transport in cardiology system.

However, there are problems associated with check valves, such as high pressure losses, sensitivity to solid particles, and wear and fatigue of moving valves. Therefore, to eliminate the need for check valves, a nozzle/diffuser configuration may be employed to substitute for the check valves and to rectify the flow. Thus, a micropump utilizing the difference of the flow resistance through the nozzle/diffuser elements to direct the flow in a preferred direction is referred herein as a "valveless micropump".

In one exemplary embodiment of the present disclosure, unidirectional rectified fluid flow is achieved without check valves by using a nozzle/diffuser passage at the inlets 20, 32 and the outlets 22, 34. The features of the valveless embodiment will be explained with reference to FIG. 3, which shows an embodiment of the second pump body 24. It should be apparent that the first pump body has identical features and has been left off for the sake of clarity. In this embodiment, inlet 32 and outlet 34 include, respectively an inlet diffuser 46 and an outlet diffuser 48 which are in fluid communication with the second chamber 26.

Referring specifically to the inlet diffuser 46, the diffuser element includes a pair of walls 50, 52 connecting the second inlet 32 with the second chamber 26. The walls 50, 52 are disposed at an angle θ and are of a length L. The walls 50, 52 define an inlet throat 54 having a width $W_1$ and an outlet end 56 having a second width $W_2$ wherein $W_2$ is greater than $W_1$. In the embodiment shown in FIG. 3, the depth of the inlet and outlet diffusers 46, 48 is the same as the depth of the second chamber 26, which has been found to allow for simplified manufacture, however other configurations are also acceptable, including a frustoconical configuration shown in FIG. 4 and a frustopyramidal configuration shown in FIG. 5

Figure 4:
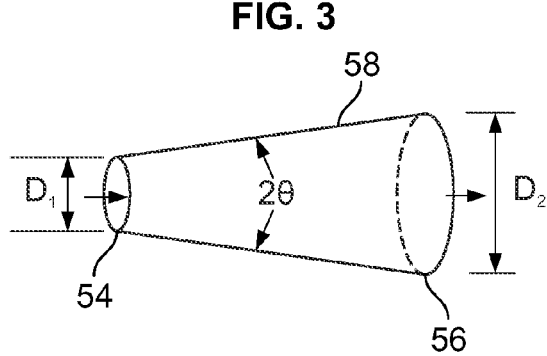
FIG. 4 is a schematic representation of a nozzle/diffuser flow element having a frustoconical configuration.
Figure 5:
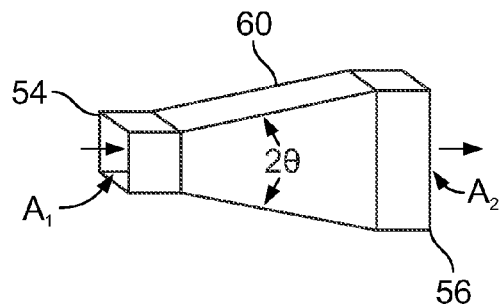
FIG. 5 is a schematic representation of a nozzle/diffuser flow element having a frustopyrimidal configuration.

The frustoconical diffuser of FIG. 4 includes an inlet throat 54 of diameter $D_1$ and an outlet end 56 of diameter $D_2$, wherein $D_2$ is greater than $D_1$. The frustoconical diffuser also includes a wall 58 disposed at an angle of 2θ. Likewise, the frustopyramidal diffuser of FIG. 5 includes an inlet throat 54 of Cross sectional area $A_1$ and an outlet end 56 of cross sectional area $A_2$, wherein $A_2$ is greater than $A_1$. The frustopyramidal diffuser also includes wall segments 60 disposed at an angle of 2θ.

Figure 6:
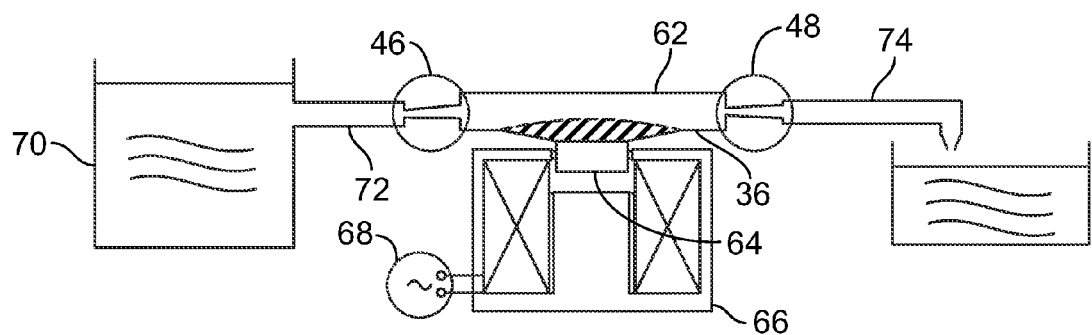
FIG. 6 is a schematic representation of a single chamber micropump illustrating the fluid flow path.

For simplicity, FIG. 6 shows a schematic representation of a micropump having a single chamber 62, a single magnet 64, and a single electromagnetic coil 66 energized by a power supply 68. Fluid contained in a fluid reservoir 70, flows through inlet tubing 72 to inlet diffuser 46, into the chamber 62 where it is pumped through the outlet diffuser 48 through outlet tubing 74 for its intended use.

Figure 7:
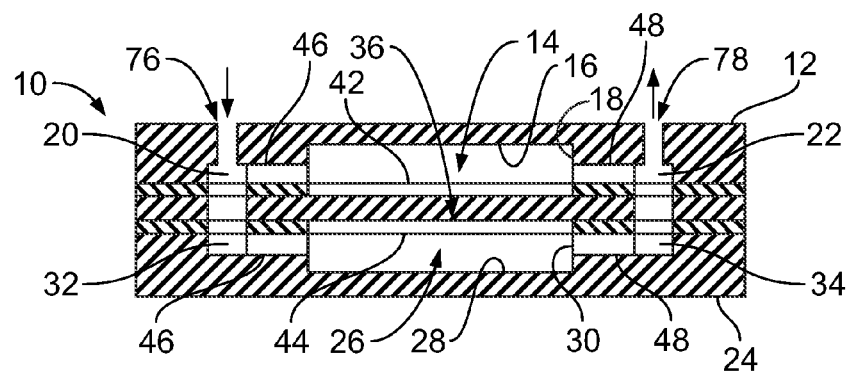
FIG. 7 is a cross section of a dual chamber micropump assembly of the present disclosure showing a combined parallel flow path.

Referring to FIG. 7, an embodiment of the valveless micropump of the present disclosure may include a combined parallel flow path, wherein the dual chamber micropump 10 is configured to with the first chamber 14 and second chamber 26 in fluid communication with a common inlet 76 and common outlet 78. Of course, as should be apparent, the embodiment of micropump 7 depicted in FIG. 7 may be configured to have separate parallel flow paths. Separate parallel flow paths would allow simultaneous flow of two different fluids.

Figure 8:
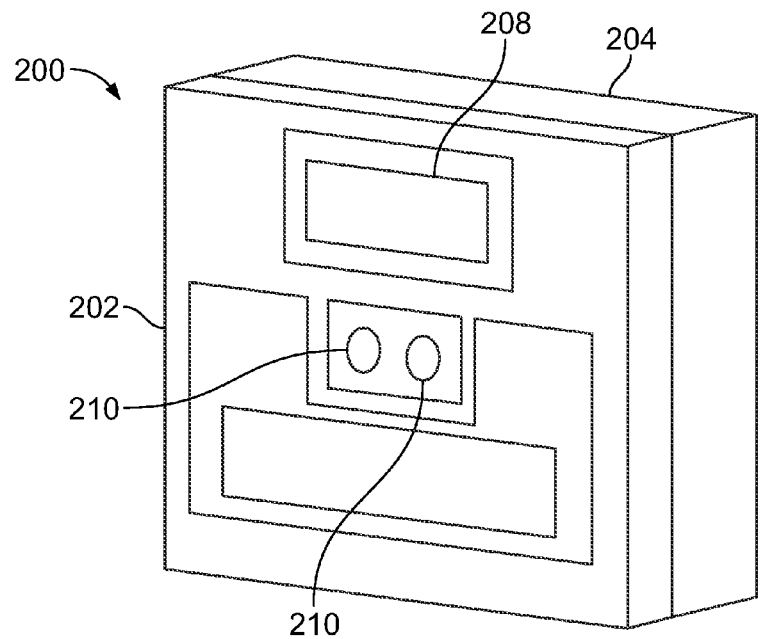
FIG. 8 is a perspective view of an embodiment of a micropump assembly of the present disclosure.
Figure 9:
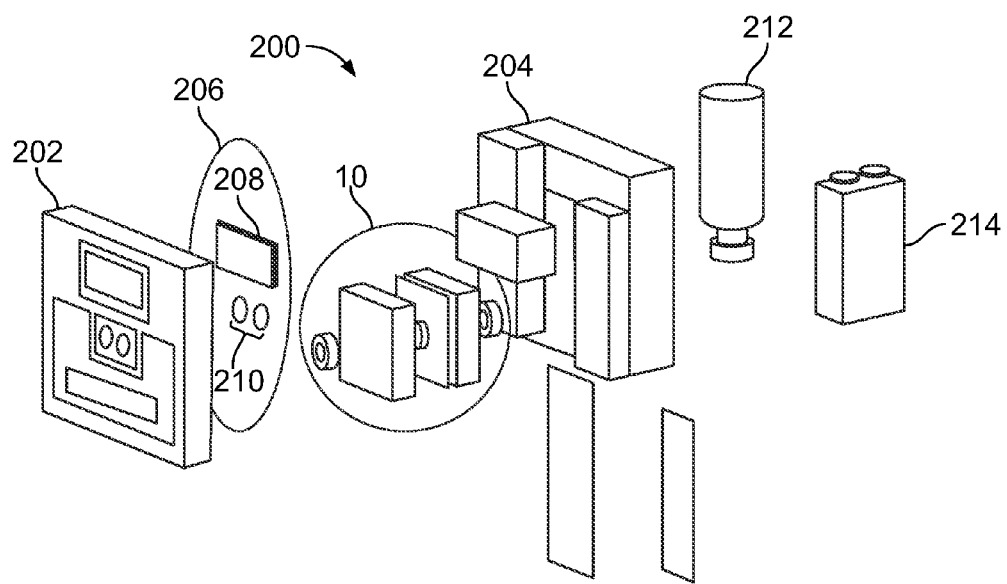
FIG. 9 is an exploded perspective view of the micropump assembly of FIG. 8.

Referring now to FIGS. 8 and 9, in another embodiment of the present disclosure, the micropump 10 as previously described is included as part of a device 200 and enclosed within a housing 202, 204. Housing 202, 204 is configured to include a controller (not shown). The controller is connected to a control panel 206 to allow a user to input operating parameters, such as flow rate. Control panel 206 includes a display 208 and one or more input buttons 210. Housing 204 is configured to receive a vial 212 which serves as the fluid reservoir for the micropump 10. In an exemplary embodiment, the vial 212 may contain insulin, or any other drug, biologic, or compound. Housing 204 is configured such that vial 212 is in fluid communication with the micropump 10 upon insertion into the housing. Housing 204 is also configured to configured to receive a battery 214 as a power supply for the actuator and controller. In the embodiment shown in FIG. 9, the battery is depicted as a standard 9V battery. However, depending on the application, other types of batteries may also be acceptable, for example a 3V coin-cell (watch) battery may be used in applications where overall size is a consideration.

Figure 10:
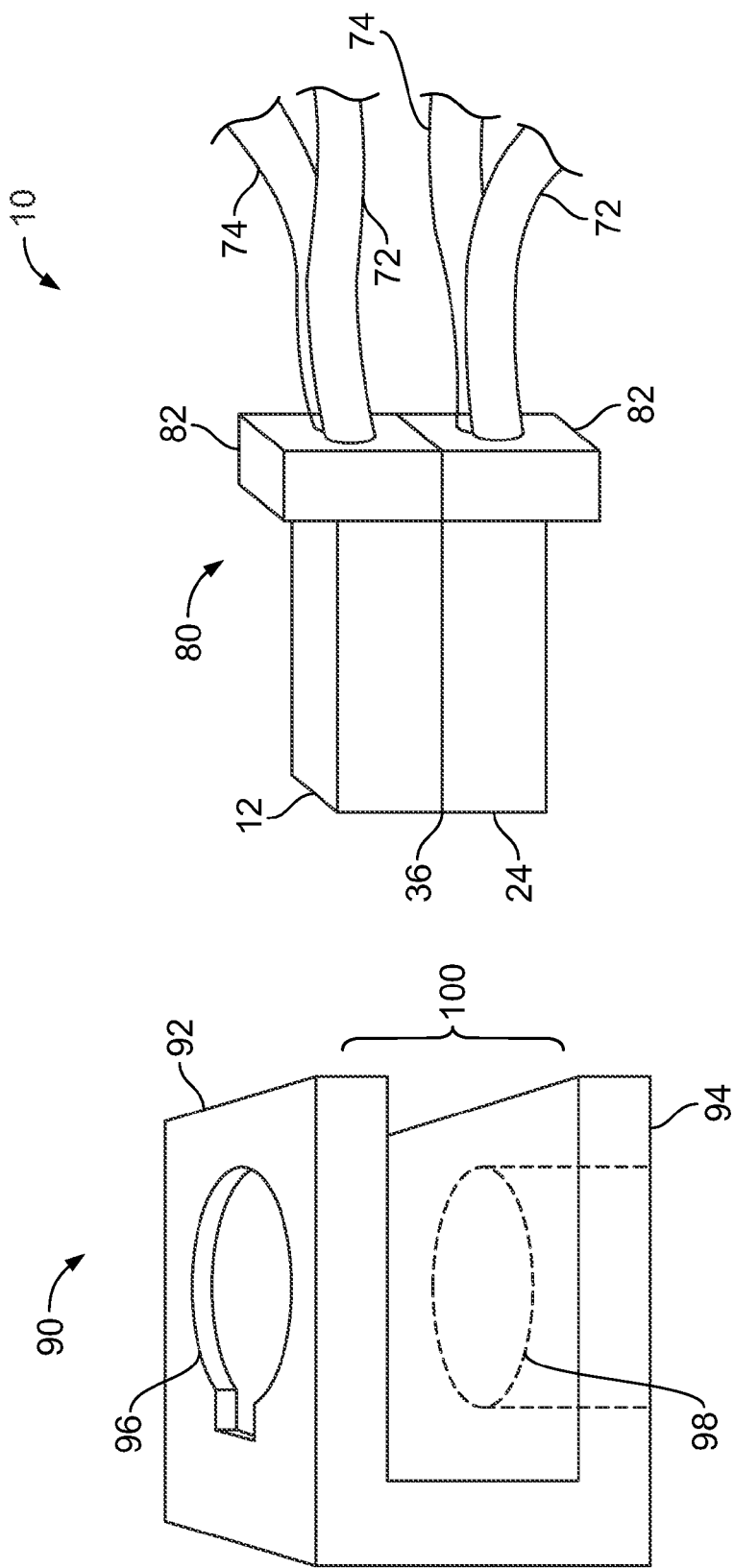
FIG. 10 is a perspective view of a micropump cartridge and actuator assembly receptacle.

Referring now to FIG. 10, the micropump 10 of FIG. 1 may be configured as a pump cartridge 80 insertable into a driver 90. Pump cartridge 80 includes a first pump body 12, a second pump body 24, and a flexible membrane 36 disposed therebetween. Pump cartridge 80 may optionally include a check valve manifold 82. Alternatively, pump cartridge 80 may be of a valveless design as disclosed herein. Inlet and outlet tubing 72, 74 is then connected to the check valve manifold, or in the case of a valveless micropump, directly to the inlets 20, 32 and outlets 22, 34 of the first and second pump bodies.

Driver 90 includes a first support 92 and a second support 94, the second support 94 being disposed separate and apart from the first support 92. The first and second supports 92, 94 each include a recess 96, 98 respectively configured to receive a solenoid or activation coil (not shown). The first and second supports 92, 94 define a receptacle 100 configured to receive pump cartridge 80.

Several proposed actuation mechanisms for micropumps have been reported already, mainly including piezoelectric, electrostatic, electromagnetic, and thermo-pneumatic and shape memory alloy, etc. The majority of the micropumps employ piezoelectric or electrostatic actuation, which operate at a relatively high frequency and require high voltage in magnitude of hundreds to thousands for minimal membrane displacements. As for the electromagnetic actuation, it demonstrates advantageous over other actuation approaches when large displacements, fast response time and relatively low power consumption are highly desired. Magnetic actuation of a membrane with integrated magnets can produce a few hundred μN and a large membrane deflection. These desired properties are highly appealing for many medical applications. Hence, the fluid-membrane coupling effect on the resonant frequency of an electromagnetically driven valveless micropump is discussed in details in the following sections.

The actuation force is applied through an oscillating membrane to drive the working medium in the pump. Therefore, reliability and performance of the micropump depend upon the dynamic characteristics of the composite membrane.

For an oscillating membrane, material properties such as the density, Young's modulus and Poisson's ratio, will significantly influence the natural frequency of the membrane. For example, in MEMS devices the majority of the membranes are integrated composite layers which include some sensing or actuating membrane layers. In this specific example, the characteristics are quite different from the individual material layers. Thus, the equivalent density of the composite layers has to be properly derived.

For a magnetically actuated membrane micropump, there are two schemes for creating the functional membrane. One is soft magnetic material electroplated or with a permanent magnet bonded on the top of the membrane several permanent magnets are manually assembled into the PDMS membrane. Then, an external magnetic field is applied either by which a permanent magnet or an integrated planar micro coil in the substrate to control the movement of the membrane. Since the dimension and layout of the bulk magnets embedded in the membrane can influence the distribution of electromagnetic force and the membrane stiffness, a composite membrane is fabricated herein with magnetic properties.

Silicon, silicon nitride and thin metal sheets are suitable as membrane materials for micropumps. For instance, a thin silicon membrane in the range of several micrometers can be realized with current micromachining techniques. However, the Young's modulus of silicon is 190 Gpa, which limits its application for the reciprocating pump. The pump membrane with flexible materials, such as parylene, polyimide, SU-8 and PDMS. These membranes require small actuating pressure and have large deflection as well as large stroke volume. In an exemplary embodiment of the present disclosure, PDMS (Silgard184, Dow Corning Corp) is used both for the micropump body and actuation membrane.

Because of its low modulus and good compatibility with silicon and glass substrates, PDMS (Sylgard 184 Silicone Elastomer, Dow Corning Corporation) is selected as the membrane material in the exemplary embodiment. Hard barium ferrite powders (UMBS-1B, Unimagnet Industry Co., Ltd, China) are mixed into PDMS (at 1:1 weight ratio) to develop an actuation membrane. The composite membrane has homogenous and isotropic material properties and can produce bi-directional deflections in an external magnetic field. Material properties for the components of an exemplary embodiment of the present disclosure are shown in Table 1.

TABLE 1

Material Properties of Membrane Components

| Parameter | Pure PDMS | PDMS composite | Fe powder |
|---|---|---|---|
| Young's Modulus | 1.8e3 | 2.56e6 | 2.11e8 |
| Density (Kg/m$^3$) | 1026.9 | 2053.8 | 7850 |
| Poisson's ratio | 0.5 | 0.5 | 0.33 |

The main challenge of the fabrication is to produce a thin composite membrane. A thin composite membrane with bulk magnet breaks easily when released from mold during the fabrication process whereas a thick membrane suffers the disadvantage of limited deflection under magnetic forces. In the exemplary embodiment, a thickness of 0.15 mm PDMS layer is spin-coated on a silicon wafer and cured at 75° C. for two hours. A magnet is placed in the middle of the first PDMS layer. Then, liquid PDMS is poured around the magnet to form a layer of 0.5 mm thickness. A glass slide is used to remove the extra PDMS. The membrane is put on a 100° C. hot plate for 30 minutes. Finally, a third 0.15 mm PDMS layer is covered on the top and cured at 75° C. for two hours.

The polarity of the composite membrane is dependent upon the polarity of the bulk magnet. Thus, the magnetic force on the membrane is reversed as the magnetic field is switched. The amplitude and frequency of the oscillating membrane are controlled by the AC square wave input currents applied on the solenoid actuator. The electromagnetic forces are measured directly for the membrane analysis. The total static electromagnetic forces with different currents on the composite membrane are measured and listed in Table 2. It shows that the attractive forces are larger than the repulsive forces because of the decrease of the air gap resulted from the attractive forces. Thus, the composite membrane will not stop moving until a balance is reached between the magnetic force and membrane's elastic force. The maximum attractive and repulsive forces on the membrane are 23.7 mN and 21.7 mN at the current of 0.2 A, respectively, which would be used to estimate the maximum deflection and stress distribution of the composite membrane by FEA.

TABLE 2

Electromagnetic Force on Membrane

| Current (A) | Repulsive force (N) | Attractive force (N) |
|---|---|---|
| 0.10 | 0.0099 | −0.0117 |
| 0.12 | 0.0123 | −0.013 |
| 0.14 | 0.0142 | −0.0151 |
| 0.16 | 0.0169 | −0.0179 |
| 0.18 | 0.0189 | −0.0204 |
| 0.20 | 0.0217 | −0.0237 |

Resonant Frequency

Figure 11:
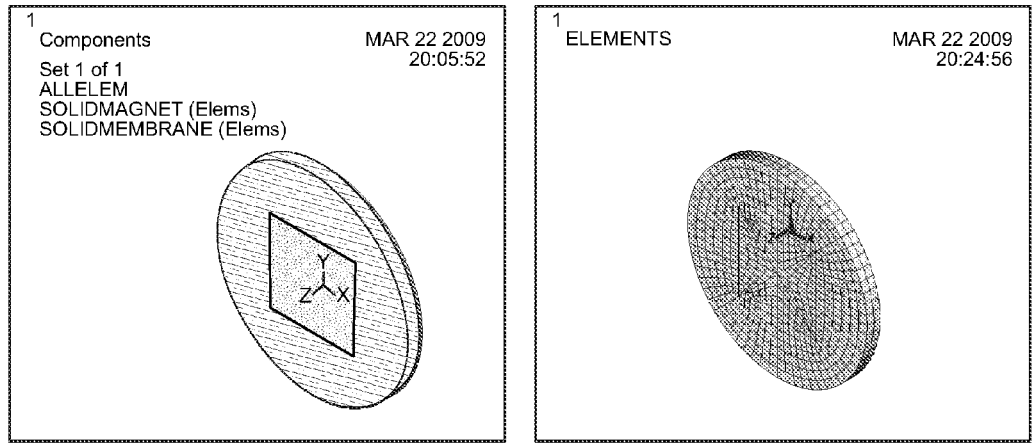
FIGS. 11-14 are plots of finite element models of an embodiment of the membrane of the micropump of the present disclosure.

Commercially available software ANSYS10.0 is used to model the composite membrane. Two types of 3D element types are mainly used: Solid 45 and Shell 63. Solid 45 is used as the elements for the bulk NdFeB magnet (thickness: 0.5 mm) embedded and the PDMS layer (thickness: 0.5 mm) around the magnet. Another two PDMS layers with a thickness of 0.15 mm covered on the top and bottom of the composite structure are meshed with element type Shell 63, shown as in FIG. 11. There are 1917 nodes and 2208 elements in this model. The material properties of the membrane used for calculation are shown in Table 3. Since the end width (0.38 mm) of the microchannels is small compared to the diameter of the membrane (7 mm), all fixed edge boundary condition of the composite membrane is assumed herein.

TABLE 3

Material Properties of Membrane Components

| Materials | Density (Kg/mm$^3$) | Young's Modulus (MPa) | Poisson ratio |
|---|---|---|---|
| PDMS | 1.0269E−6 | 0.75 | 0.449 |
| NdFeB | 6.667E−6 | 151 | 0.24 |

Figure 12:
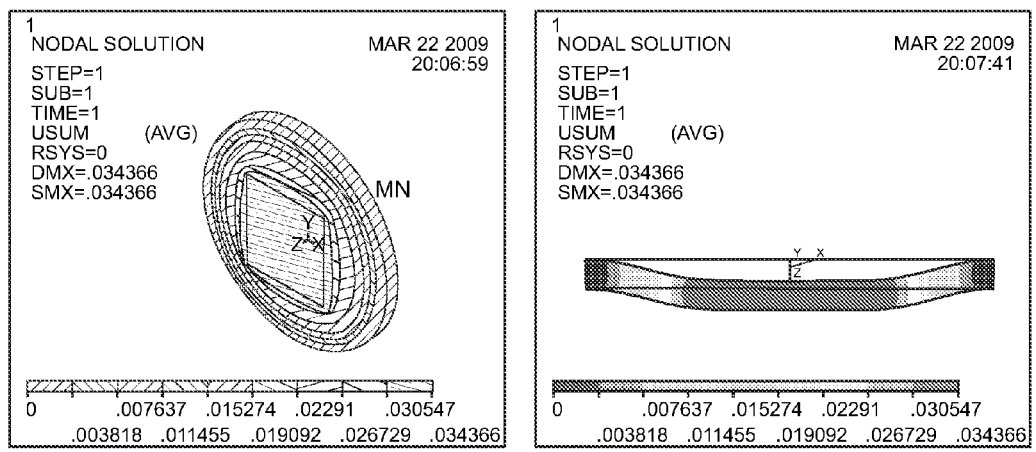
Figure 13:
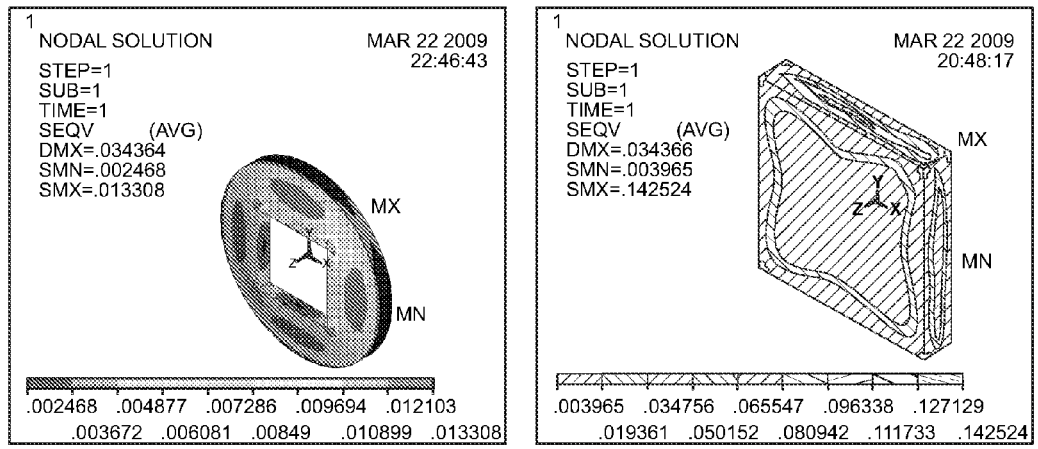

A trapezoidal cross-section and a maximum deflection 34.34 μm of the composite membrane are observed in FIG. 12. This value is less than the depth of the fluid chamber. Thus, the membrane does not touch the bottom of the chamber, especially when the fluid is loaded and the fluid resistance takes effect on the membrane. Because of different material properties of the composite membrane, the magnetic force is concentrated on the bulk magnet area. The stress distribution of the membrane is shown in FIG. 13. The concentrated stress areas are basically distributed on the four corners of the magnet because of the square shape of the bulk magnet. The maximum stress in the membrane is about 0.1425 MPa, which is less than the shear stress of PDMS material. The static analysis of the membrane ensures the safety and reliability of micropump operation.

Figure 14:
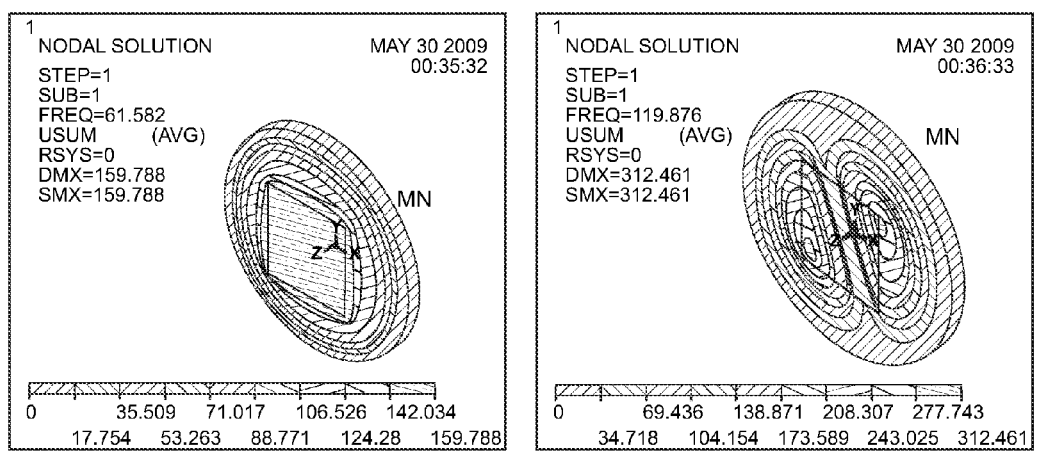
Figure 15:
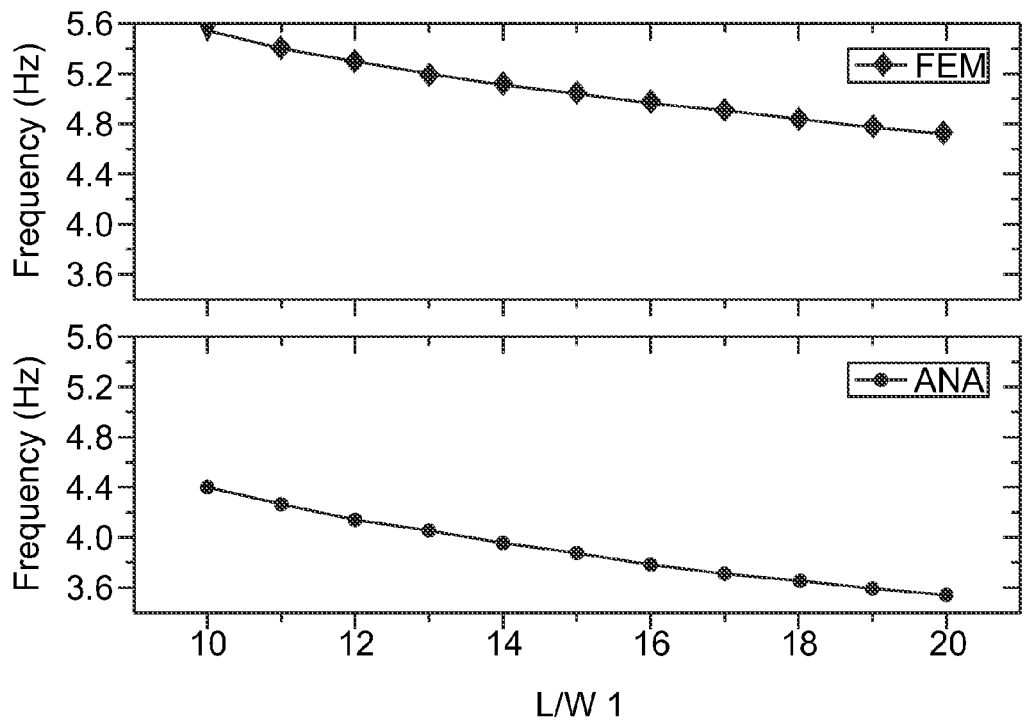
FIG. 15 is a plot of resonance frequency varying with diffuser slenderness ratio for an embodiment of a valveless micropump of the present disclosure.
Figure 16:
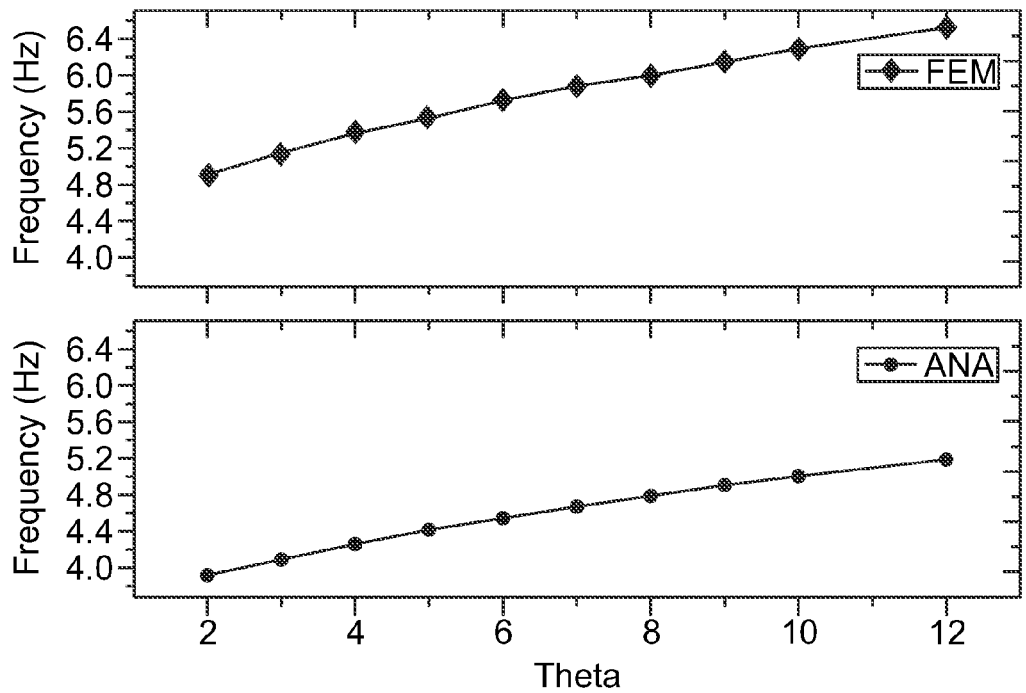
FIG. 16 is a plot of resonance frequency varying with diffuser open angle for an embodiment of a valveless micropump of the present disclosure.
Figure 17:
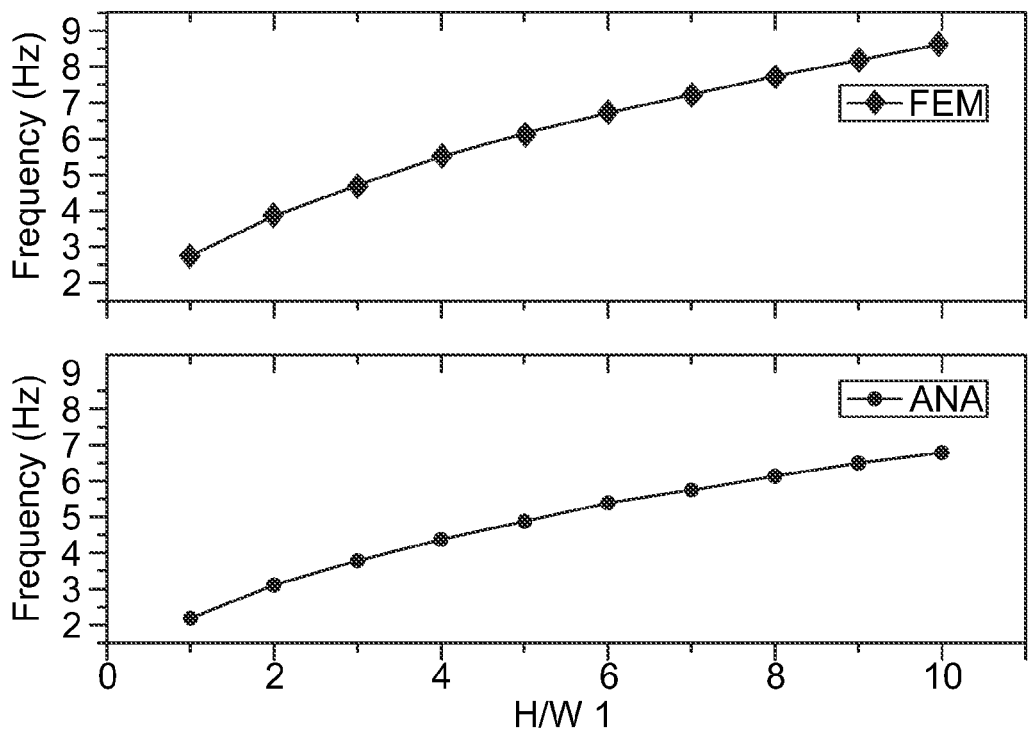
FIG. 17 is a plot of resonance frequency varying with diffuser high aspect ratio for an embodiment of a valveless micropump of the present disclosure.
Figure 18:
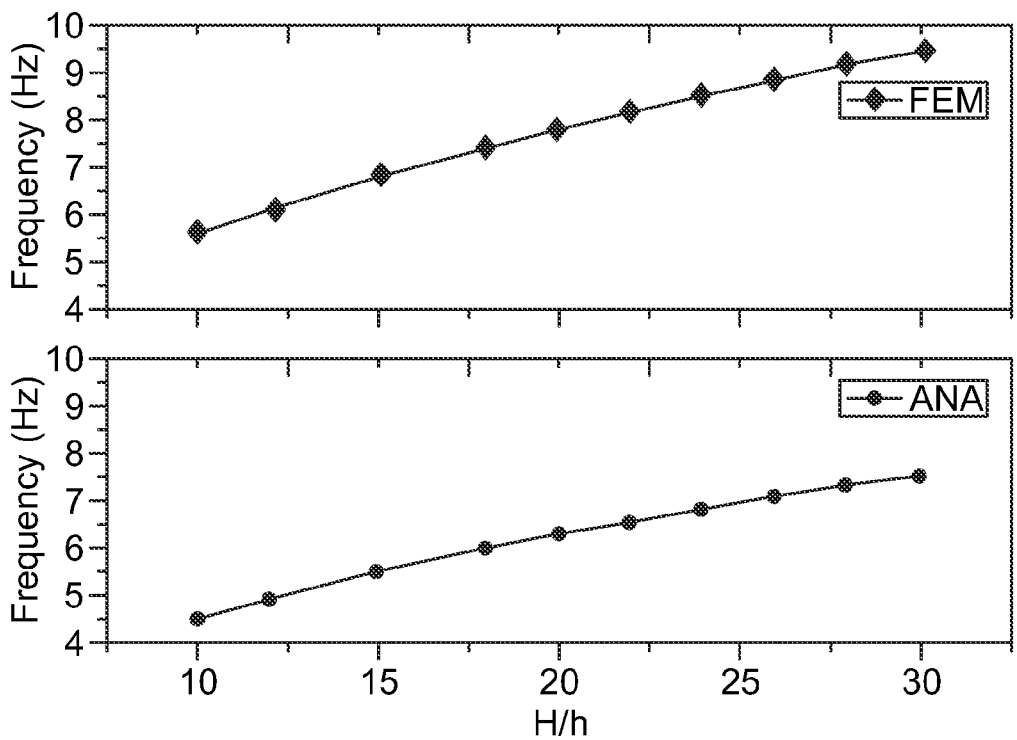
FIG. 18 is a plot of resonance frequency varying with thickness ratio of chamber depth and membrane thickness for an embodiment of a valveless micropump of the present disclosure.

FIG. 14 shows the first and second mode shapes of the flexible membrane. Observe that the membrane bends in one direction in the fundamental mode and the peak occurs in the middle area because of the embedded bulk magnet. There are two peaks for the second mode, one is up and the other one is down. As the maximum stroke volume is required to obtain high pumping flow rate, the first mode is preferred. This analysis also explains why the flow rate under second vibration mode is lower the former. When fluid is loaded in the chamber, the resonant frequency is reduced due to the added mass and damping effect on the dynamic characteristics of the membrane.

This approximation of the resonant frequency may be simplified by using a mass-spring analogy where the elastic properties of the membrane are represented by the spring and the fluid in the chamber is represented by the mass. However, the discrepancy between calculated and measured frequency is as large as 36% (calculated and measured frequencies: 734 Hz, 540 Hz; 4238 Hz, 3350 Hz, respectively). It neglects the nonlinear behavior in the nozzle/diffuser elements leading to the overestimation of the resonant frequency. An approximated model couples the membrane vibration and fluid in the pumping chamber and nozzle/diffuser elements based on a set of partial differential equations. The membrane-fluid coupled governing equation of a thin circular membrane having thickness h, mass density $\rho_m$ is:

$$D\nabla^4 w + \rho_m h \partial^2 w/\partial r^2 = f_e - p \quad (1)$$

Where $D=Eh^3/12(1-v^2)$ is the flexural rigidity;
$\nabla^2 = \partial^2/\partial r^2 + (1/r)\partial/\partial r + (1/r^2)\partial^2/\partial \theta^2$ is the Laplacian operator in the polar coordinate; v and E are the Poisson ratio and Young's modulus, respectively.

The deflection of the membrane is reasonably small compared to the characteristic length of the membrane. Thus, the small deflection theory of the thin plate is still applicable in the membrane micropumps. The plate is assumed to be made of linearly elastic, homogeneous and isotropic material and effects of shear deformation are neglected. The solution takes the form:

$$w(r, \theta, t) = \sum_{m=0}^{\infty} \sum_{n=0}^{\infty} W_{mn}(r)\cos(m\theta)e^{j\omega_{mn}t} \quad (2)$$

Where $W_{mn}(r)=A_{mn}J_m(\lambda_{mn}r/R)+B_{mn}Y_m(\lambda_{mn}r/R)+C_{mn}I_m(\lambda_{mn}r/R)+D_{mn}K_m(\lambda_{mn}r/R)$. In which m and n are the numbers of nodal circles and diameter lines; $A_{mn}$, $B_{mn}$, $C_{mn}$, and $D_{mn}$ are the mode shape constants that are determined by the boundary conditions. $J_m$, $Y_m$ are the Bessel functions of the first and second kinds, and $I_m$, $K_m$ are the modified Bessel functions of the first and second kinds R is the radius of the membrane.

On the fluid side, we consider the fluid flow as an incompressible laminar flow. Further, we assume that the fluid loading does not alter the modal shape although it will add effective mass and damping. Therefore, the Navier-Stokes equation and mass continuity equation are used to describe the fluid flow inside each element illustrated in FIG. 3.

$$\rho\left(\frac{\partial \vec{u}}{\partial t} + \vec{u} \cdot \nabla \vec{u}\right) = -\nabla p + \mu \nabla^2 \vec{u} + p\vec{g} \quad (3)$$

$$\nabla \cdot \vec{u} = 0 \quad (4)$$

Wherein $\vec{u}=(u,v,w)$ is the fluid velocities in x, y, z directions. The dynamic pressure p represents coupling of the membrane vibration and the fluid flow during the pumping phase.

The volume flow through the inlet and outlet can be denoted as $Q_n$ and $Q_d$ from inside to outside. The pressure loss can be expressed as $\Delta p = \xi \rho \bar{u}^2/2$ where $\xi$ is the loss coefficient and $\bar{u}$ is the mean flow velocity through the throat area of the nozzle/diffuser elements. The deflection of the membrane w leads to a variation of fluid volume expressed as:

$$V(p,t) = \iint w(r,\theta,t)drd\theta \quad (5)$$

The rate of volume change thus given by:

$$\dot{V}(p) = Q_n + Q_d \quad (6)$$

For the special case, there is no pressure difference, the input pressure is zero, and the excitation force is assumed to be sinusoidal. Solving equations (1)-(6), the original expression of the resonant frequency considering the fluid effects is derived in [11] and can be rewritten as the form:

$$f_1 = \frac{f_0}{\sqrt{1+\beta}} \quad (7)$$

$$\beta = \frac{\rho}{\rho_m}\left[\frac{H}{h} + \frac{(1+\alpha^2)LA_m}{2h\sqrt{A_1A_2}}\right] \quad (8)$$

$$f_0 = \frac{10.21h}{2\pi a^2}\sqrt{\frac{E}{12\rho m(1-v^2)}} \quad (9)$$

$$A_1 = HW_1 \quad A_2 = HW_2 \quad (10)$$

$$\frac{W_2}{W_1} = 1 + \frac{2L\tan(\theta)}{W_1} \quad (11)$$

Where $\beta$ is corresponding to the ratio between effective fluid mass and membrane mass, which relates the fluid and membrane density ratio, the area of vibration membrane $A_m$, and the dimensional variables of the diffuser element (the chamber height H, the length of diffuser element L and the throat section width W, shown as in FIG. 3). Where $f_0$ is the fundamental frequency of a thin plate of clamped edge. Therefore, equation (7) implies that the resonant frequency of the membrane micropump is relevant to the modal properties of the membrane, the density ratio between the fluid and membrane, and geometry and size of the micropump.

Combination of acoustics and structural mechanics modules in COMSOL modeling software by COSMOL AB of Stockholm, Sweden, can deal with the problem of coupled fluid-elastic structure interaction. In multiphysics coupling, the acoustic analysis provides a load (the pressure) to the structural analysis, and the structural analysis provides accelerations to the acoustic analysis. Here, the pressure is related to the density through the speed of sound in the fluid. It is assumed that the membrane is clamped at the outer edge, in which the displacements and velocities are zero. When the membrane is bending under the electromagnetic field, the acoustic pressure from the fluid is acting as a normal load. For the fluid part, we assume that the substrate of the micropump is a perfect rigid wall, thus the normal acceleration vanishes at the walls of diffuser/nozzle elements and at the fluid chamber walls. Non-slip condition is set at fluid-wall interface and no pressure boundary conditions are set at the inlet and outlet. All the boundary conditions are set the same as discussed previously.

Equations (7)-(11) suggest that many influence parameters will contribute to the variation of the resonant frequency. Thus, it is necessary to establish dimensionless variables using Buckingham Π theorem to identify these factors.

$$f_1 = f(L/W_1, \theta, H/W_1, H/h) \quad (12)$$

Where $L/W_1$ is defined as the diffuser slenderness ratio; $\theta$ is the diffuser open angle; $H/W_1$ is the diffuser high aspect ratio; $H/h$ is the thickness ratio. Thus, in order to directly demonstrate the relationship between the resonant frequency of the membrane micropump with fluid-membrane coupling and the geometrical influence parameters, analytical and numerical solutions are plotted in FIGS. 15-18 after W and h are specified. Water is used in this example.

As shown in FIGS. 15-18, an inverse proportional relationship between the resonant frequency and diffuser slenderness ratio ($L/W_1$) and a proportional relationship between the resonant frequency between open angle (20), high aspect ratio ($H/W_1$) and thickness ratio are observed in both finite element method and analytical solutions. Furthermore, the FEA solutions are in good agreement with the analytical predictions in magnitude. The analytical solutions are within 20% of the FEA solutions. For comparison, this discrepancy can be reduced to as low as 10% when air is loaded for the test. Based on aforementioned analysis, dimensions of a specific micropump model (without check valves) are chosen in Table 4 and properties of the working fluid at room temperature are listed in Table 5.

TABLE 4

Dimensions of a Micropump Embodiment

| Parameter | Value |
|---|---|
| PDMS composite membrane thickness h (μm) | 65 |
| Circular fluid chamber radium a (μm) | 3000 |
| Fluid chamber depth H (μm) | 650 |
| Diffuser/nozzle throat width $W_1$ (μm) | 160 |
| Diffuser/nozzle end width $W_2$ (μm) | 440 |
| Diffuser/nozzle open angle (2θ) | 10 |
| Diffuser/nozzle depth HI (μm) | 650 |
| Diffuser/nozzle length L (μm) | 1600 |

TABLE 5

Parameters for Working Fluid Calculations at Room Temperature

| Parameter | Air | Water |
|---|---|---|
| Speed of sound (M/s) | 343 | 1500 |
| Density (Kg/m$^3$) | 1.2 | 1000 |
| Viscosity (N · s/m$^2$) | 1.8e−5 | 0.001 |

The first two resonant frequencies of this actuation membrane are about 138.106 Hz and 287.222 Hz when no fluid is loaded. When air is loaded, the resonant frequencies are slightly reduced to 104.762 Hz and 284.198 Hz. When water is used for the test, the frequencies are 5.531 Hz and 65.269 Hz, respectively. This comparison indicates that an increase in density added mass to the system results in a decrease in resonant frequency and the higher fluid density is, the more apparent the damping effect. It is observed that the circular membrane bends in one direction under the first resonant frequency and has one peak in the middle of the membrane, which is preferred in micropump actuation. This is in agreement with the assumption that the fluid loading does not alter the modal shape.

Figure 19:
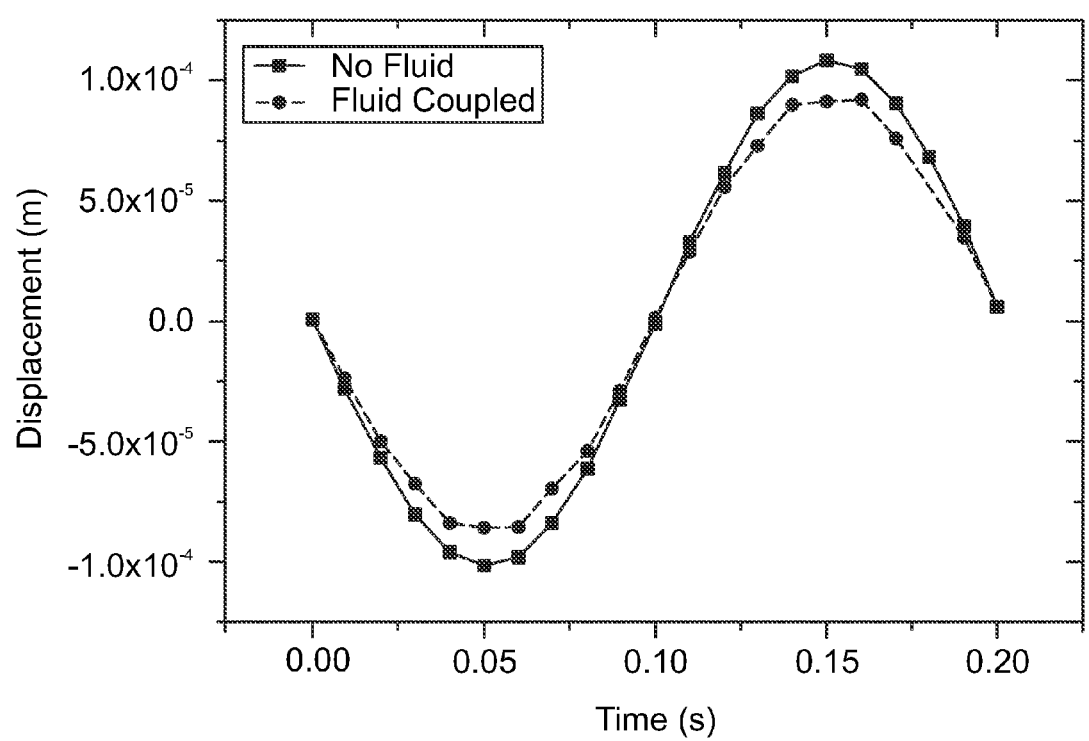
FIG. 19 is a plot of membrane displacement versus time for an embodiment of the micropump of the present disclosure.
Figure 20:
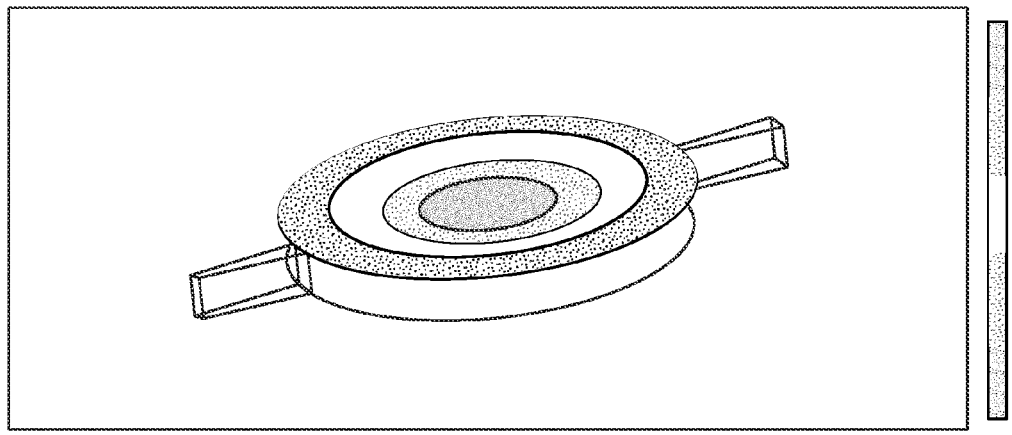
FIG. 20 is a finite element model of an exemplary embodiment of a valveless micropump of the present disclosure showing maximum displacement in discharge mode.
Figure 21:
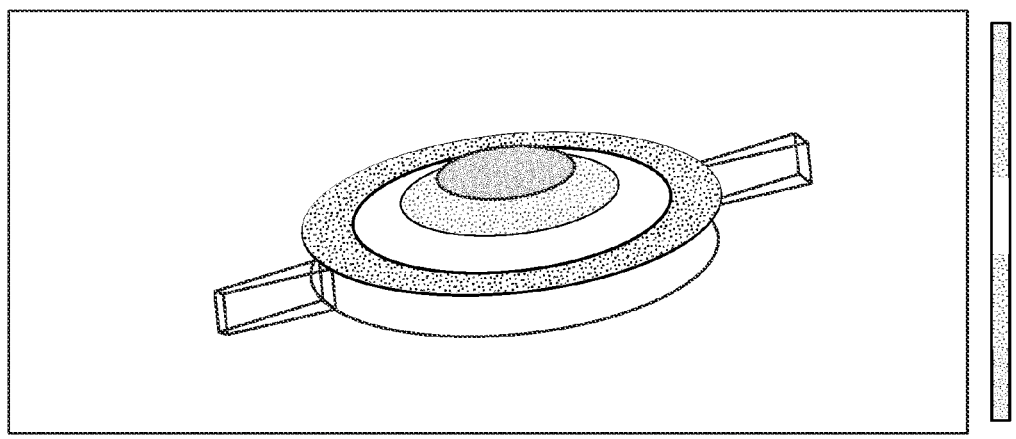
FIG. 21 is a finite element model of an exemplary embodiment of a valveless micropump of the present disclosure showing maximum displacement in suction mode.

Another angle of view to prove that the fluid damping effect occurs during pumping action is the membrane displacement. A transient analysis of the micropump is conducted in a period of time and the comparison of the actuation membrane with fluid damping or no fluid loaded is shown in FIG. 19. At 0.05 s and 0.15 s, the maximum displacement of the membrane occurs in opposite directions and the micro device is in pump and supply modes shown as in FIG. 20 and FIG. 21, respectively. The deflection amplitude of the actuating membrane is 87.691 μm at a 0.4 A excitation current, less than 104.5 μm when there is no fluid coupled in the chamber. Thus, the deflection amplitude of membrane is reduced by 16.09%. This again implies that the fluid damping effect occurs during the pumping action.

A rigid fluid chamber with microchannels, but flexible actuation membrane for the device is desired for better performance and reliability consideration. A soft and flexible polymer chamber will cause vibration throughout the whole micropump. Increasing the curing agent percentage in the mixture increases the rigidity of the PDMS. Therefore, curing agent in the PDMS mixture is added to a ratio of about 5:1 PDMS to curing agent to provide a rigid substrate for the fluid chamber. The ratio for the membrane is 10:1 PDMS to curing agent. Then, liquid PDMS is poured to a SU-8 mold and cured to obtain the desired microstructure. Finally, two layers are carefully aligned and pressed together.

As for the bonding techniques, normal working condition, such as room temperature and regular pressure, is preferred for a low-cost fabrication. Several different PDMS bonding techniques have been reported and compared regarding to their bonding strength as the multilayer PDMS micro devices attracts increasingly interest in the past few years. Quick, but expensive oxygen plasma bonding still is the widely used method for bonding PDMS layers whereas uncured PDMS adhesive provides an effective and simplified replacement for oxygen plasma bonding. Both of these methods are acceptable for assembling the actuation membrane and fluid chamber substrate of the embodiments of the present disclosure. A very thin film of uncured PDMS is applied to the surface of the molded fluid chamber PDMS substrate on a 100° C. hot plate for 20 minutes. Alternatively, oxygen plasma treatment (Spacemaker II®, microwave oven, 10% oxygen for 10 seconds) also provided a very strong bonding method between two PDMS layers to seal a fluid chamber and inlet/outlet micro channels. The weight of the micropump is measured about 1.47 g.

Figure 22:
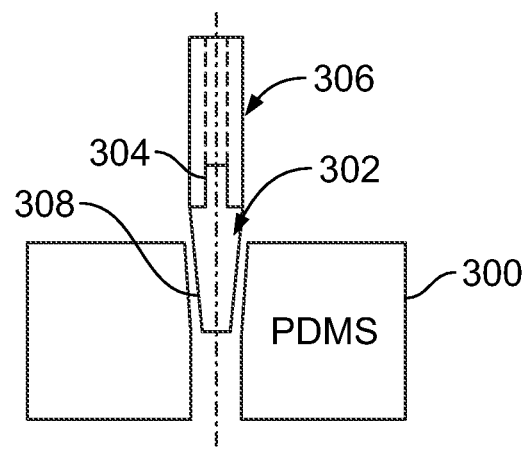
FIG. 22 illustrates a microfluidics connector for use with the micropump of the present disclosure.

After the micropump is assembled, another challenge faced is the interconnectivity between the microdevice and the standard fluidic equipments, such macro syringes and tubing. Microfluidics involves dimensions on the order of millimeters or smaller and thus there is no readily available microfluidic connection to accommodate different size tubings. PDMS connector 300 that includes a hole through the center and double-sided adhesive to connect to the microfluidic device and a plastic fitting 302 is fabricated by CNC machining, shown in FIG. 22. Fitting 302 includes one small end 304 connected with tubing 306 and the other conical end 308 is pressed into the soft-polymer device.

The average volumetric flux over a period is one of the most important characteristics of micropumps. Inertial effects and energy losses in the nozzle/diffuser elements and fluid chamber as well as losses in the actuation membrane are taken into account herein. Frequency-dependent flow rate was derived based on the fluid-membrane coupling governing equations (1)-(4) and fluid volume equations (5)-(6).

$$\overline{Q} = \frac{1}{2n}\int_0^{2\pi} Q_d \, dt \tag{13}$$

$$= \frac{\alpha F}{\pi} \sqrt{\frac{6\pi C_1}{\sqrt{(16\beta C_3 F)^2 + 9\pi^2(1-C)^4 + 3\pi(1-C)^2}}}$$

Where:

$$C_1 = \left(\frac{\omega}{\omega_0}\right)^2, \quad C_2 = C_1 R_\rho \left(\frac{H}{h} + \frac{L}{h}\frac{A_m}{2\sqrt{A_1 A_2}}\right), \tag{14}$$

$$C_3 = \frac{R_\rho C_1}{8}\left(\frac{A_m}{A_1}\right)^2, \quad C_4 = C_3 \frac{4L}{h}\frac{A_1}{A_m}\sqrt{\frac{A_1}{A_2}}$$

$$C = C_1 + C_2 + \alpha^2 C_4,$$

$$\alpha = \left(\sqrt{\xi_n} - \sqrt{\xi_d}\right)/\left(\sqrt{\xi_n} + \sqrt{\xi_d}\right),$$

$$\beta = 2\xi_n \xi_d / \left(\sqrt{\xi_n} + \sqrt{\xi_d}\right)^2, \quad \omega_0 = 2\pi f_0$$

The term $C_1$ represents the inertia effect of the membrane; $C_2$ considers the inertial force of the fluid inside the pump; $C_3$ reflects the viscous losses effects in the nozzle/diffuser element; $C_4$ represents the inertial effects of the fluid inside the nozzle/diffuser elements; C associates all inertial contributions of fluid and membrane. F is the dimensionless actuation force and there is no pressure difference between the inlet and outlet. If parallel dual fluid chambers configuration is employed, shown as in FIG. 10, the terms $C_2$, $C_3$, and $C_4$, are doubled correspondingly.

The theory developed above indicates that the ratio between the pressure loss coefficients ($\xi_n/\xi_d$) should be as high as possible in order to maximize the pumping stroke efficiency. Therefore, the nozzle/diffuser pump could generate a net flow from the nozzle to the diffuser for each pumping cycle. From these equations, we observe that the flow rate is influenced by three factors, the ratio ($\omega/\omega_0$) of excitation frequency and membrane's fundamental frequency, the density ratio ($R_\rho$) and the geometric size ratio which determines the loss coefficients ($\alpha$ and $\beta$). However, it should be mentioned that the pressure loss coefficients ($\xi_n=1.01$ and $\xi_d=0.449$) are derived numerically by using finite element analysis (FEA) at low Reynolds number since the pressure drop is mainly dependent upon the dimensionless variables according to the Buckingham $\Pi$ theorem. Again:

$$\xi = f(L/W_1, \theta, H/W_2, 1/Re) \tag{15}$$

Meanwhile, to a certain extent, surface roughness inside the nozzle/diffuser elements is also contributing to the pressure drop. However, it is unnecessary to accurately measure the geometrical sizes of the micro nozzle/diffuser and calculate loss coefficients if the micropump has been already fabricated and flow rate can be measured directly. Hence, the FEA is an effective approach to calculate the loss coefficients and predict the pumping flow rate during the concept design stage. Based on the analysis in section 3 and the actual requirements of excitation frequency, a valveless micropump with desired dimensions shown in Table 4 is used to study the frequency-dependent performance.

Figure 23:
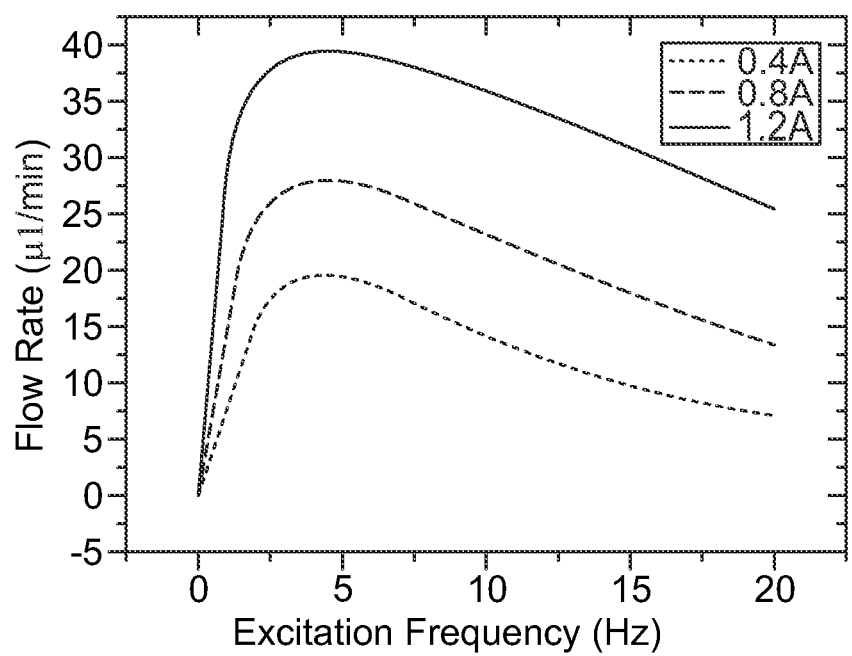
FIG. 23 is a plot showing that maximum pumping flow rate is dependent on the excitation frequencies for different actuation currents.
Figure 24:
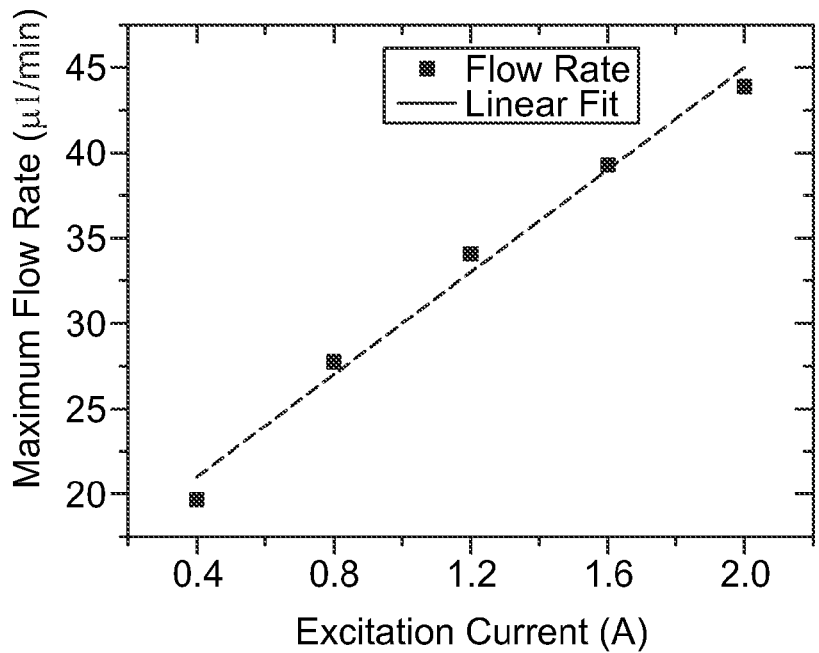
FIG. 24 is a plot of maximum flow rates for different actuation current amplitudes.
Figure 25:
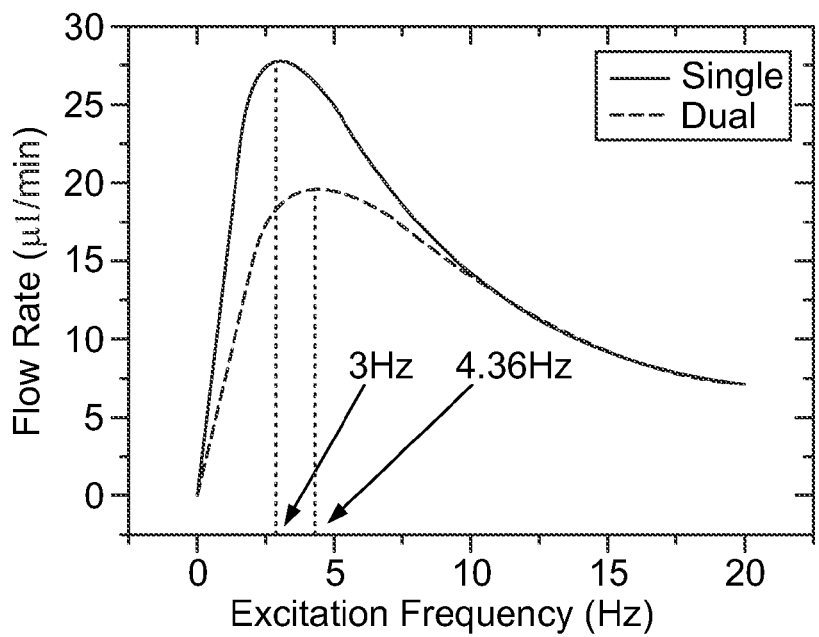
FIG. 25 is a comparison of maximum pumping flow rate.

The graph shown in FIG. 23 demonstrates that the pumping flow rate of the micropump is a function of the excitation frequency varying from 0 Hz to 20 Hz. The flow rate increases almost linearly with the excitation frequency at low frequency range and then reaches a maximum flow rate at the resonant frequency of the actuating membrane with the fluid damping. After the flow rate peak, the pumping rate decreases sharply at higher frequencies. Referring to FIG. 24, the maximum pumping rate increases linearly with actuation voltage amplitudes. The maximum flow rates at 0.4 A and 2 A are 19.64 μl/min and 43.86 μl/min, respectively. The increase of the voltage amplitude leads to the increase of the membrane deformation. In order to satisfy high flow rate requirement, for example, in a drug delivery system, keeping the same input power energy, a parallel dual-chamber configuration is illustrated in FIG. 7. However, it is interesting that although the fluid capacity is doubled for the latter, which works in counter-phase, the maximum flow rate is around 27.73 μl/min under the condition of 0.4 A input current with an excitation frequency of 3 Hz. This is less than twice of 19.64 μl/min of the former operated under the same magnitude of current, but with an excitation frequency of 4.36 Hz shown as in FIG. 25. The result is also reasonable as the fluid inside both chambers will take effect.

In an exemplary embodiment of the micropump of disclosure, a low-cost simple solenoid is developed for magnetic actuation instead of integrating micro coils to avoid complex and rigorous fabrication process. Although the structure of the external magnetic actuator imposes limitations for its applications, electromagnetic actuation still demonstrates advantageous over other actuation approaches in the cases where large forces, fast response and low power consumption are highly desired whereas the size is the secondary consideration element. Simple design and easy fabrication, the electromagnet consists of an electromagnetically inductive coil wound around a soft iron cylindrical rod (5 mm dia.×10 mm), and a movable membrane with a small bulk NdFeB magnet (dimension: 3×3×0.5 mm$^3$ and a weight of 0.03 g, by Neotexx, of Berlin, Germany) integrated. Although typically weak over a very short distance, electromagnetic driver can create controllable magnetic fields directly by an actuation circuit. Thus, alternating attractive and repulsive forces on this composite membrane are induced when the magnetic field is reversed, which produce periodically deflections of the membrane.

Figure 25A:
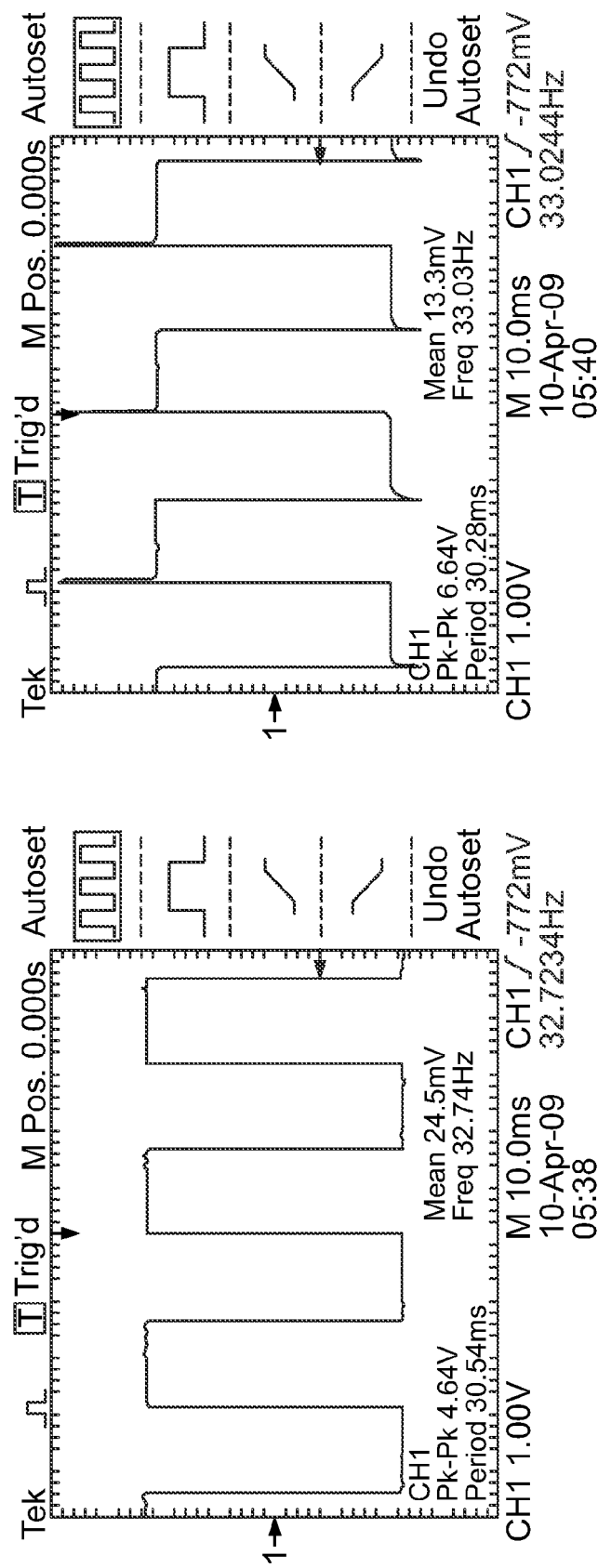
FIG. 25A is a plot of a square wave excitation signal before and after actuator loading.

The resistance and inductance of copper coils (28AWG, 460 turns) is about 4.40Ω and 3.49 mH under 100 Hz condition. Current above 0.5 A in the solenoid generates heat very quickly. Thus, the practical current of actuation should be controlled under 0.5 A. Two types of actuation current are commonly used: sinusoidal and square wave currents. With the same peak-to-peak value, the square wave current can maintain large deflection and carry more energy which can be converted into magnetic force. A DC power supply which can provide a maximum −30/+30V voltage (BK Precision 1672) and a square wave generator circuit may be used to produce square wave current, shown in FIG. 25A. The square wave signal changes a little after the solenoid actuator is loaded due to the inductance of the coils. The DC supply which can be substituted by batteries has a potential for portable application of the micropump. The frequency of the signal can be controlled by fine tuning the resistance of a potentiometer in the circuit.

The vertical electromagnetic force $F_z$ acting on a permanent magnet by conducted coils is given by $$F_z = B_r \int_z^{z+h_m} S_m \cdot \frac{\partial H_z}{\partial z} \cdot dz \tag{16}$$

Where $H_z$ is the vertical component of the magnetic field produced by the coil, $B_r$ is the remanence of the magnet and $S_m$, $h_m$ are the surface area and thickness of the magnet, respectively. $\partial_z/\partial Z$ is the gradient of the magnetic field. This equation indicates that the electromagnetic force is proportional to the change in the vertical magnetic field and the magnet volume.

In an exemplary embodiment of the micropump of the present disclosure, the design parameters listed in Table 6 were used.

TABLE 6

Micropump Structural Dimensions

| Design Parameter | Micropump (μm) |
|---|---|
| Membrane thickness (h) | 800 |
| Fluid chamber radius (a) | 3500 |
| Fluid chamber depth (H) | 500 |
| Diffuser/nozzle throat width (W1) | 160 |
| Diffuser/nozzle end width (W2) | 440 |
| Diffuser/nozzle open angle (Theta)° | 10 |
| Diffuser/nozzle length (L) | 1600 |

According to the requirement of flow rate in the applications, the volume stroke and the excitation frequency can be estimated for a certain membrane and thus the magnetic force required for actuation and electric input signal also can be derived during the design stage. However, it is not very practical to estimate these parameters by experiment. Thus, a frequency-dependent flow rate equation is used to roughly estimate these parameters because the geometry features of the membrane, fluid chamber structure, microchannels and the fluid properties determine the resonant frequency, thus relate the flow rate of the micropump.

$$Q = 2\eta \Delta V f \quad (17)$$

Wherein, $\Delta V$ is the stroke volume, $$\eta = \frac{\sqrt{\eta_F} - 1}{\sqrt{\eta_F} + 1}$$

is defined as the pump stroke efficiency while $\eta_F$, is the diffuser rectification efficiency and f is the excitation frequency.

Then, the design parameters are determined as in Table 1 in this device. It is worth noting that increasing the stroke volume and decreasing the dead volume improves the performance of the pump. The total volume of this pump is 0.01924 ml with a diameter of 7 mm and a depth of 500 μm.

For an exemplary embodiment of the present disclosure, Ethanol is used as the working fluid. The physical properties of the medium at 20° C. and 1 atm are listed in Table 7. In this example, the setup consists of a fluid reservoir (syringe), the micropump, an actuation circuit board and electromagnetic actuator, as well as an optical microscope with CCD camera. The microscope is utilized to observe ethanol inside the fluid chamber and the bubbles generated during the pumping process.

TABLE 7

Fluid Properties at 20° C. and 1 atm.

| Working fluid | Density (g/ml) | Viscosity (m²/s) | Surface Tension (mN/m) | Boiling Temperature (° C.) |
|---|---|---|---|---|
| Ethanol | 0.789 | 1.20 × 10⁻³ | 22.39 | 78.4 |

Inlet and outlet tubing are commercially available TYGON® tubing. The inlet tubing is connected to the fluid reservoir. When the fluid is moving forwards, the fluid reservoir automatically primes the fluid chamber. Self-priming capability and bubble tolerance can be determined from the compression ratio (the ratio between the volume stroke $\Delta V$ and the total dead volume V of the pump). Because the total volume V of the micropump is constant when the micropump was fabricated, the volume stroke determined the compression ratio. In this case, the compression ratio was about 0.068 less than the minimum compression ratio 0.075 for self-priming and bubble-tolerant liquid micropumps.

During the micropump operation, the fluid flow in the outlet tube and weight of fluid are measured. The friction of the tubing to the fluid flow is of particular importance. It is necessary to consider the pressure drop in the tubing. Often the concerned flow rates of micropumps for biomedical applications are less than 1 ml/min and the Reynolds number can be estimated as 8.72. Thus, the flow passing the tubing is a laminar flow. The variation of pressure due to the friction losses in the inlet/outlet tubing can be evaluated by Hagen-Poiseuille equation as:

$$\Delta p = -\frac{128 \mu \Delta L Q}{\pi a^4} \quad (18)$$

Where $\Delta p$ is the flow resistance and $\mu$ is the fluidic viscosity and $\Delta L$, a are the length and inside radius of the tubing, Q is the flow rate.

The pressure drops of each fluid medium can be negligible (length of tubing in the test about 5 cm, pressure drops about 2.1 Pa) and will not significantly influence on the performance of the micropump.

Figure 26:
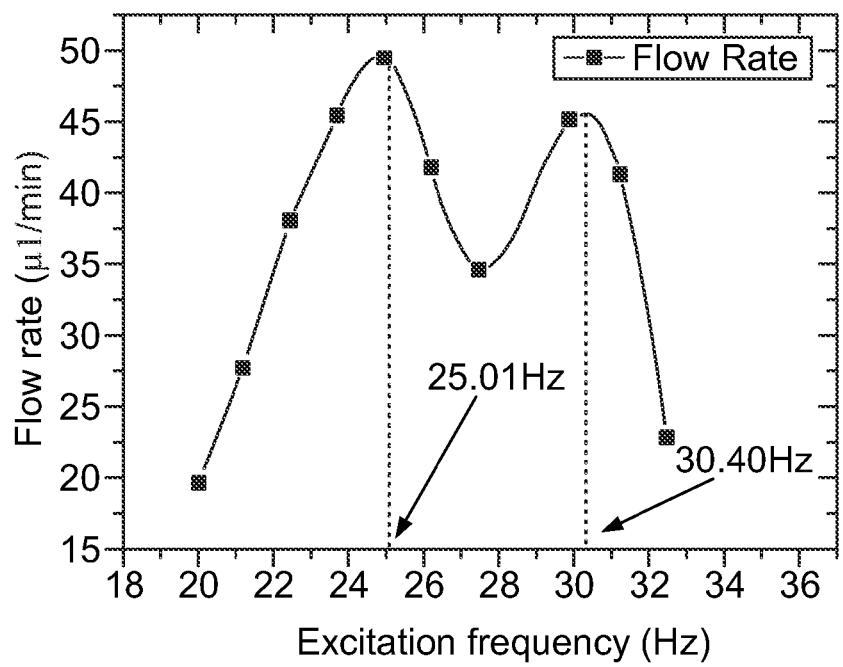
FIGS. 26-28 are plots showing flow rate varying with excitation frequency.
Figure 27:
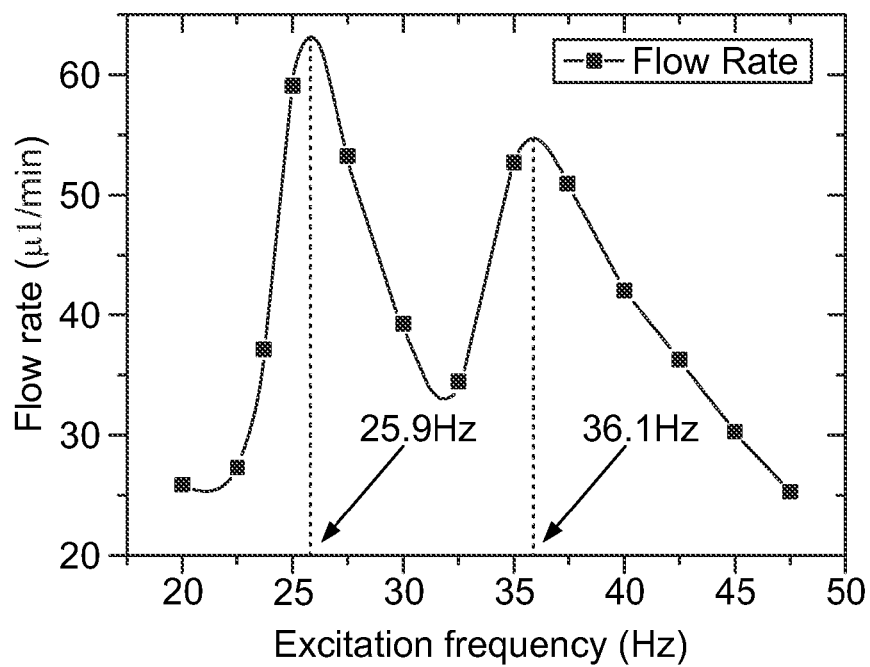
Figure 28:
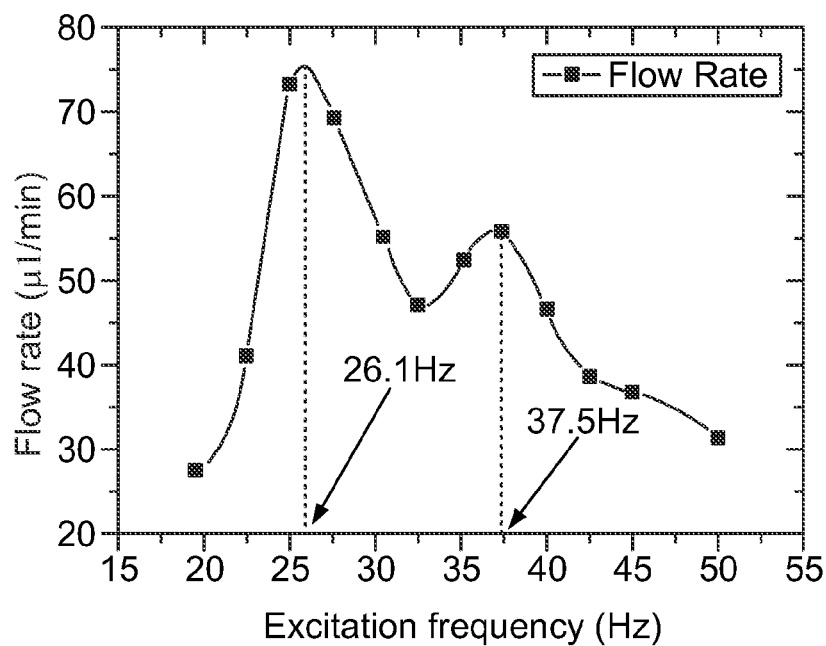

The maximum flow rate is the flow rate when the pump is working at zero back pressure. There is no pressure difference between the inlet and outlet for these different currents testing. Micropumps operating at resonant frequency can result in an increased displacement, higher flow rates and higher conversion efficiencies, thus reducing power requirements. Therefore, controlling effective excitation frequency of the system becomes very important. Currents of 0.14 A, 0.16 A and 0.18 A are used for testing the flow rates in a range of excitation frequencies. The results are illustrated in FIGS. 26-28.

The flow oscillates around a position close to the beginning of the outlet tubing which is connected to the micropump and the pump fails to transport the fluid when the frequency is below 15 Hz. This is because of the low fluidic impedance in both directions and thus valveless pumps suffer a certain the back flow. Therefore, if the excitation frequency too low, it is difficult to accumulate enough net fluid flow from inlet to outlet. Further, the fluid flow is pulsatile and difficult to maintain a constant flow rate when the driving frequency is below 20 Hz in this valveless rectification pump. This results from the periodic nature of the square wave signal applied in the magnetic actuation. Moreover, there are two flow rate peaks for these three groups of examples. This is because the first two modes of resonant frequencies of the vibrating membrane are reached.

As shown in FIG. 14, the membrane only bends in one direction whereas half of the membrane bends up and the other half bends down. The first mode creates higher volume stroke than the second mode. Therefore, usually the flow rate at second peak is lower than the first peak.

There is some difference in the flow rate curves of these three groups of testing with different current amplitudes. First, effective working frequency ranges from 20 Hz to 34 Hz for stable flow rates and the two resonant frequencies are 25.01 Hz and 30.04 Hz, respectively, for the first group. 20 Hz to 47.5 Hz and 20 Hz to 50 Hz are the frequency ranges for the second and third groups, respectively. The two resonant frequencies are 25.9 and 36.1 Hz for the second group, and 26.1 and 37.5 Hz for the third group. The values of the latter two groups are very close whereas the first group is a little deviated. Because the flow rate is small at the current of 0.14 A and friction in the tubing becomes a dominant factor, the measurement error is higher than other two groups. Second, the flow rate increases with the excitation frequency before the first flow rate peak is reached and then followed by a sharp decrease. A second peak, which is a little lower than the first peak, comes again with an increase of excitation frequency. Third, the flow rate decreases as the frequency increases. The results imply that the flow rates can be controlled within the excitation frequency of interest.

Backpressure usually refers to the pressure opposed on a free moving flow by obstructions in a fluidic system. Thus, in the micropump of the present disclosure the maximum backpressure ($P_{max}$) is defined as the opposing pressure exerting on the fluid when the flow rate of the pump becomes zero.

Figure 29:
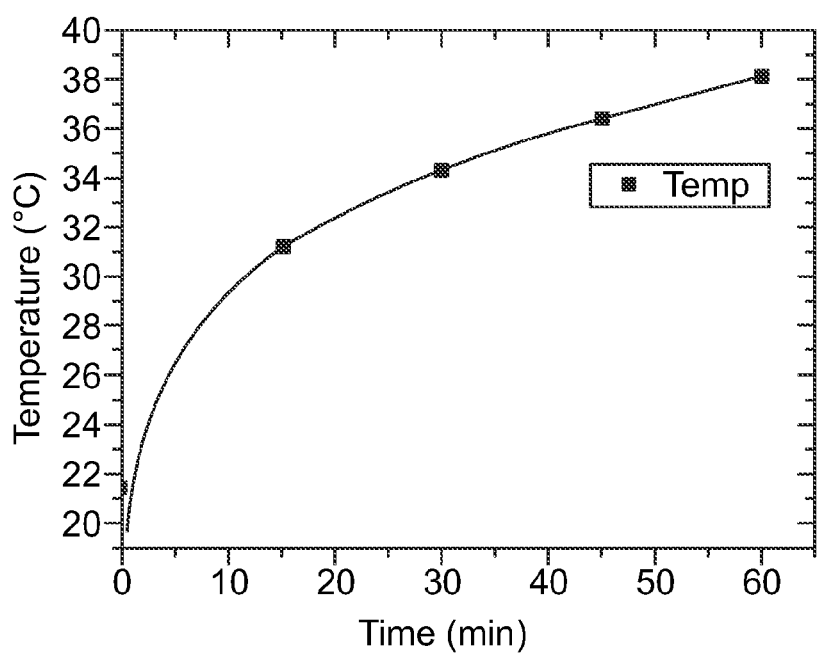
FIG. 29 is a plot of actuator temperature over time.

Achieving a constant continuous pumping in a long period is an important index of a reliable micropump. A temperature rise in the fluid chamber is an important characteristic because small bubbles generated in the chamber might significantly affect the flow rate. Moreover, high temperature might damage fluids that contain living cells or sensitive particles in biochemistry or life science applications. However, it is not easy to measure the temperature change inside the fluid chamber. Rather, the temperature rise of the magnetic actuator is measured to estimate the fluid temperature since the magnetic actuator is current-driven and the temperature of coils will be increased quickly. The real temperature of fluid should be a little lower than the temperature of the magnetic actuator. Thus, the temperature rise in one hour is measured with an excitation frequency of 25 Hz (the resonant frequency) at 0.18 A and an air gap about 1 mm between the electromagnet and the oscillating membrane. As shown in FIG. 29, the temperature steadily increased in a non linear curve from 21.3° C. to 38.1° C. This temperature is well below the critical temperature for most biological fluid samples. The characteristics of an embodiment of the micropump of the present disclosure are listed in Table 8.

TABLE 8

Micropump Characteristics

| | |
|---|---|
| Outer dimension | 11 × 7 × 2.5 mm$^3$ |
| Actuation | Electromagnetically-actuated |
| Particle tolerance | Yes |
| Resonance frequency | 25.9 Hz |
| Maximum flow rate | 75.13 µl/min |
| Maximum backpressure | 400 Pa |
| Current | 0.18 A |
| Voltage | 2.1 V |
| Power consumption | 378 mW |

Thus, an embodiment of a magnetically actuated soft-polymer (PDMS) micropump has been presented in this example. The fluid flow directing relies on two nozzle/diffuser elements which have different fluidic resistance in the inlet and outlet of this microdevice. There are several advantages associated with this micropump embodiment. The simple fabrication process and planar structures features allow easy integration into the µTAS devices thereby miniaturization of the whole microfluidic system. All the fabrication processes can be implemented outside clean-room facility, which significantly reduces the cost. Besides, the requirement of low voltage and power consumption makes the micropump of the present disclosure suitable for the use in portable medical devices, which can be powered by small batteries. The constant continuous flow rate and low temperature rise in a long period prove the feasibility of this soft PDMS micropump in biomedical applications with good reliability and biocompatibility, based on presented design and fabrication methods.

Figure 30:
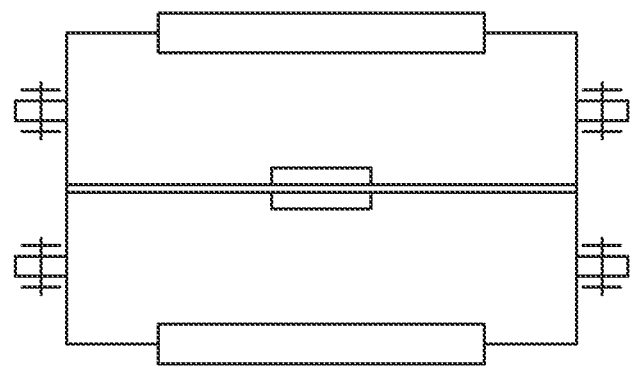
FIGS. 30-32 are schematic representations of an embodiment of the micropump of the present disclosure during operation.
Figure 31:
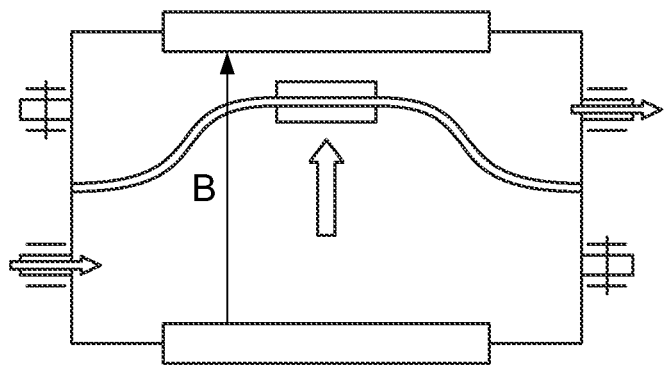
Figure 32:
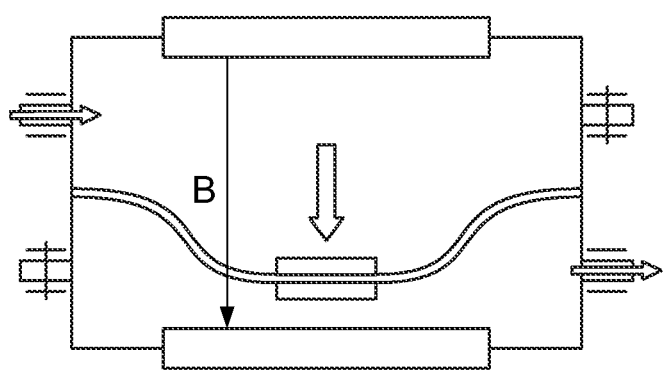

In the micropump of the present disclosure, the control system includes a sensor and a controller. The sensor being a Hall effect sensor placed in proximity to the actuator coil. Referring to FIGS. 30-32, the flexible membrane moves in reaction to the applied magnetic field (B) of the electromagnetic coils. The position of the magnets—and thus the deflection of the membrane and the respective volumes of both chambers—modifies the magnetic field configuration, which is sampled by the Hall effect sensor. A suitable sensor is, by way of example, an A1301 linear Hall effect sensor manufactured by Allegro Microsystems having a sensitivity of 2.5 mV/Gauss. The position information is provided to a controller and is used to determine the position of the magnets to within an accuracy of 0.05 mm.

The controller dictates the motion of the magnets based on the user selected flow rate requirements. Several modes of operation may be configured, such as a low speed mode for accurate dosing or a high speed mode for high volumetric flow rates.

The ability to measure the real-time position of the magnet is important because it enables closed-loop flow rate control, it prevents collisions between the magnets and chamber walls, which eliminates collision damage and reduces noise, and it enables high efficiency controlled resonance operating modes. Since the micropump of the present disclosure consists of two separate parts, a contact-less sensing system is necessary. It has been found that determining the position of the magnets, and thus the membrane, is easily accomplished in a cost effective manner by measuring the magnetic field produced by the magnets. The main drawback to implementing this method is the magnetic noise due to the electromagnetic driver coils, which needs to be suppressed. Therefore, the sensor is positioned such that magnetic noise is minimized.

Figure 33:
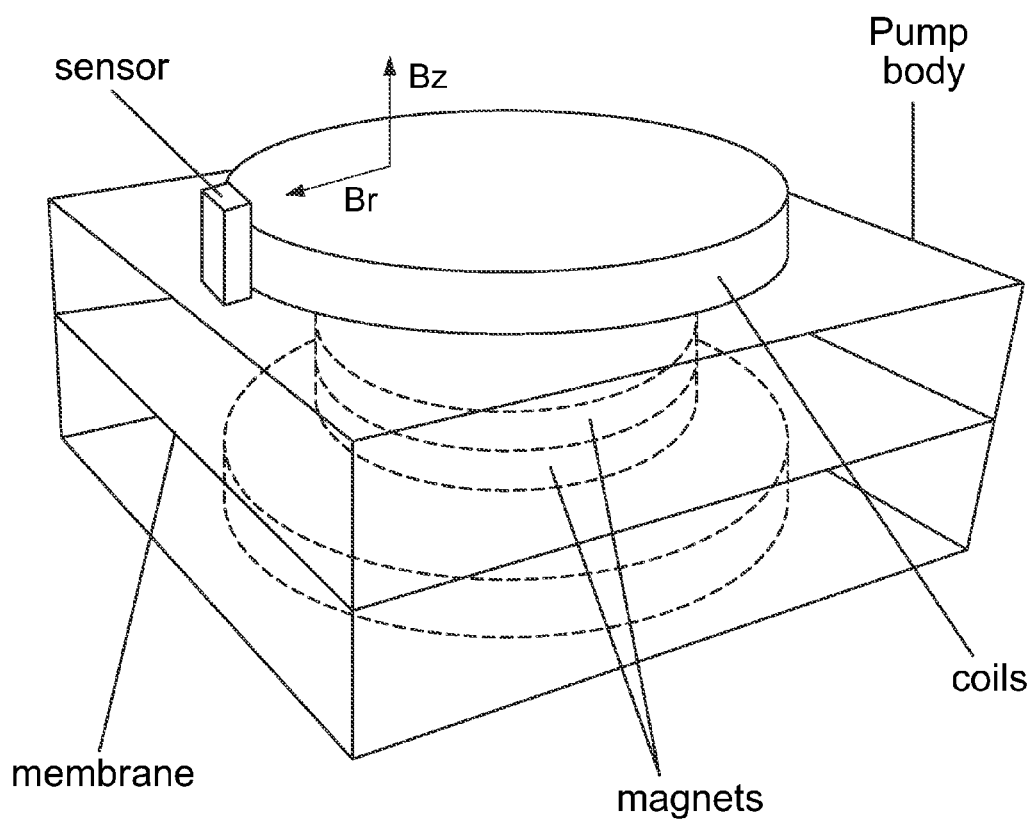
FIG. 33 is a schematic representation of the placement of a magnet position sensor.
Figure 34:
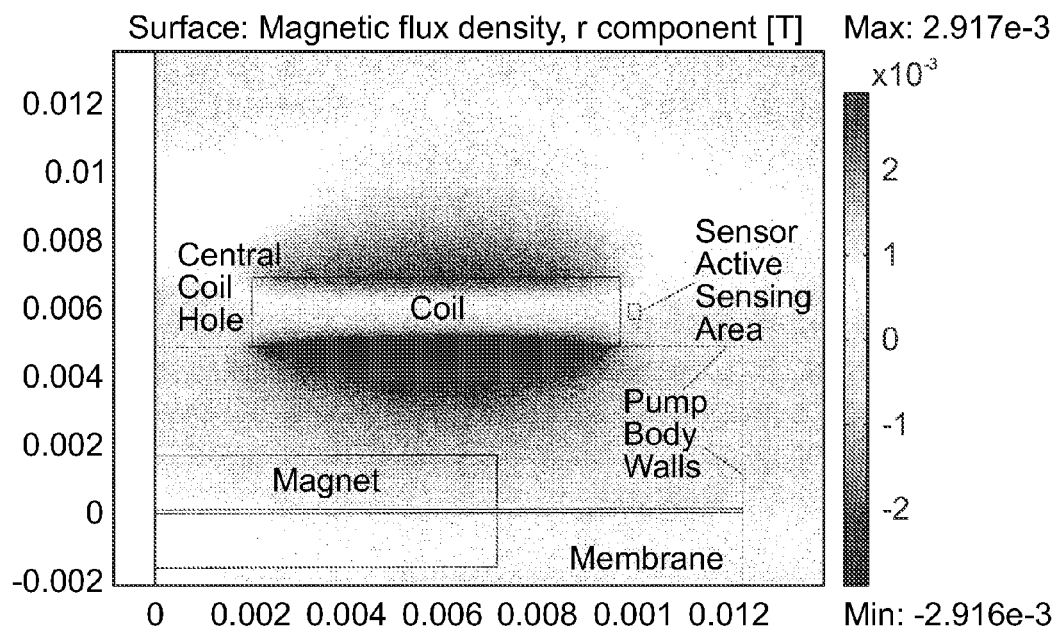
FIGS. 34 and 35 are representative plots of magnetic field density for the actuator coil and magnets, respectively.
Figure 35:
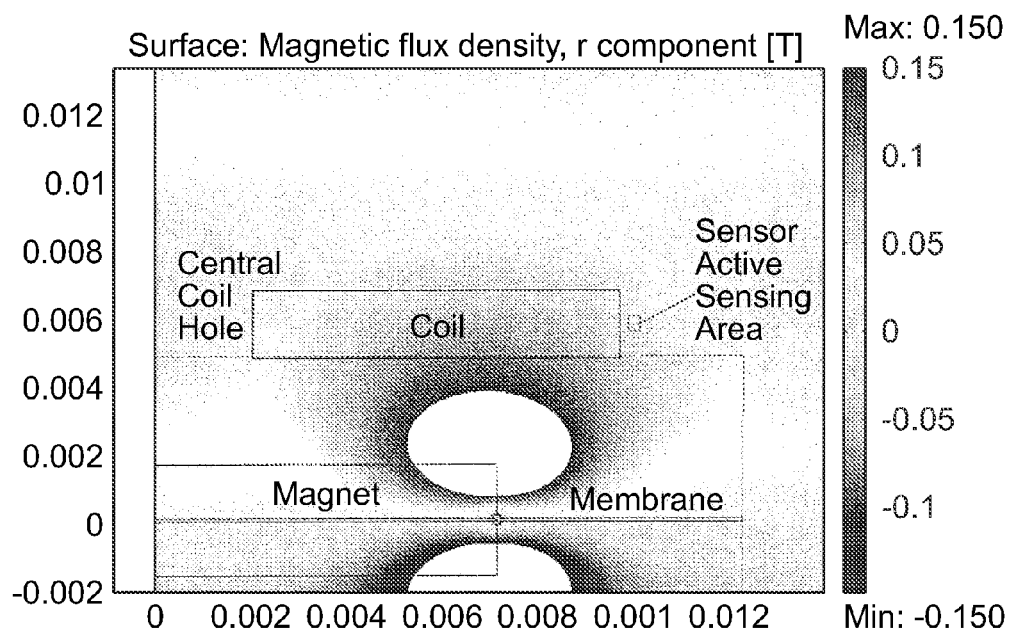
Figure 36:
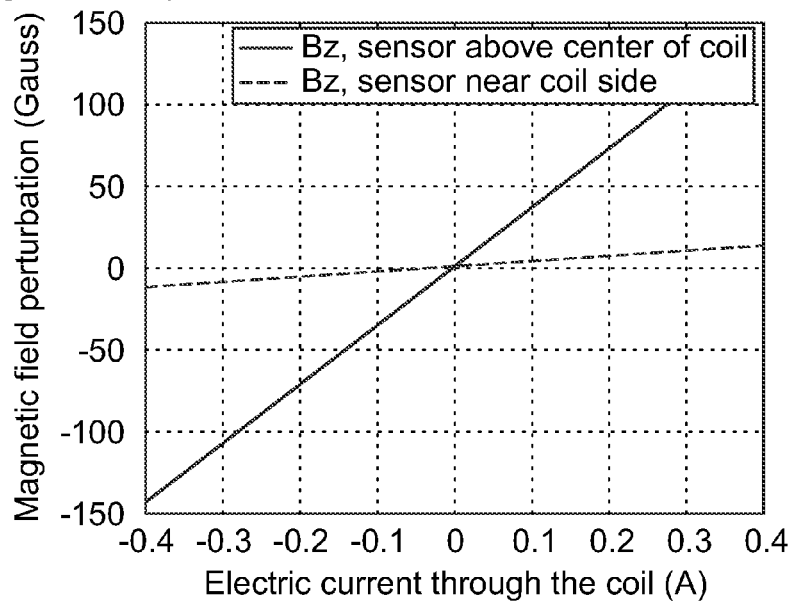
FIG. 36 is a plot of magnetic field perturbation.

The amplitude of the signal and of the magnetic perturbations depends strongly on the position and orientation of the sensor. At the sensor location, the coil magnetic field has to be the lowest possible, and the magnet magnetic field has to be the highest possible. There is a position which satisfies both requirements (see FIGS. 33, 34, 35). Along the side of each coil, $Br_{coil}$ is weak whereas $Br_{magnet}$ is strong. This location is referred to as the side location. This location provides a much better signal to noise ratio than any other possible location for magnetic field sensing. In FIG. 36 the magnetic fields created by the coil and the magnet are compared: (i) Br at the side location and (ii) Bz at the classical standard location (i.e. the center of the coil).

Figure 37:
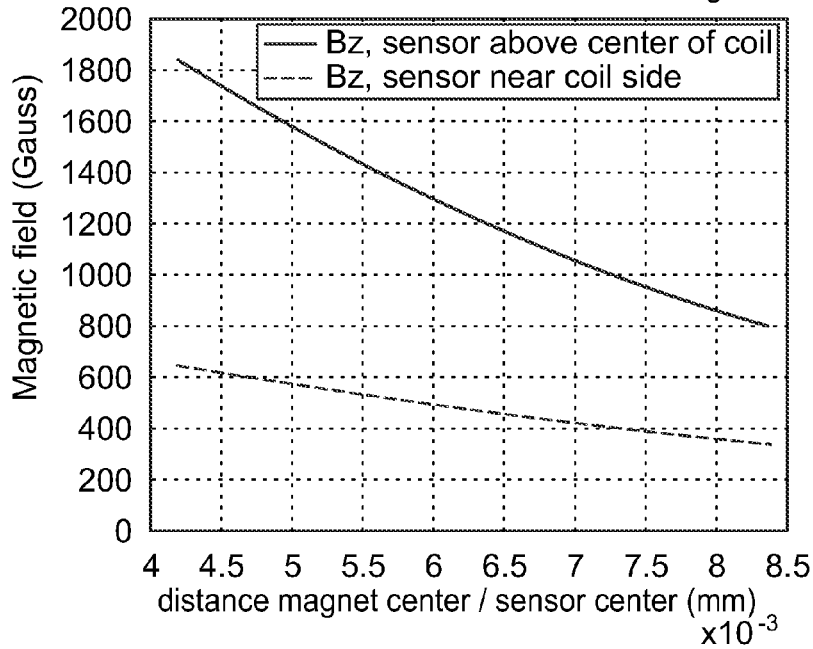
FIG. 37 is a plot of magnetic field intensity.

This side location proves to be very insensitive to the magnetic field of the coil $B_{coil}$ and still sensitive to the magnetic field of the magnet $B_{magnet}$. On FIG. 37, it is shown that the signal at the side location is approximately 3 times less than it would be at the center; however, the perturbation of the coils is about 12 times less, so that the signal/noise ratio is better at the side location.

Figure 38:
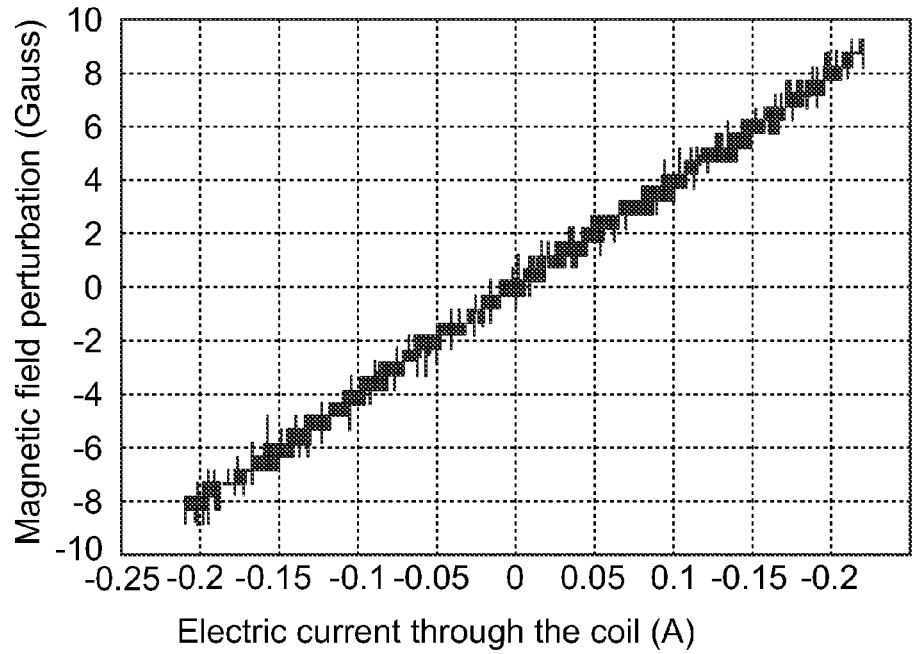
FIG. 38 is a plot of magnetic field perturbation measured by the sensor.
Figure 39:
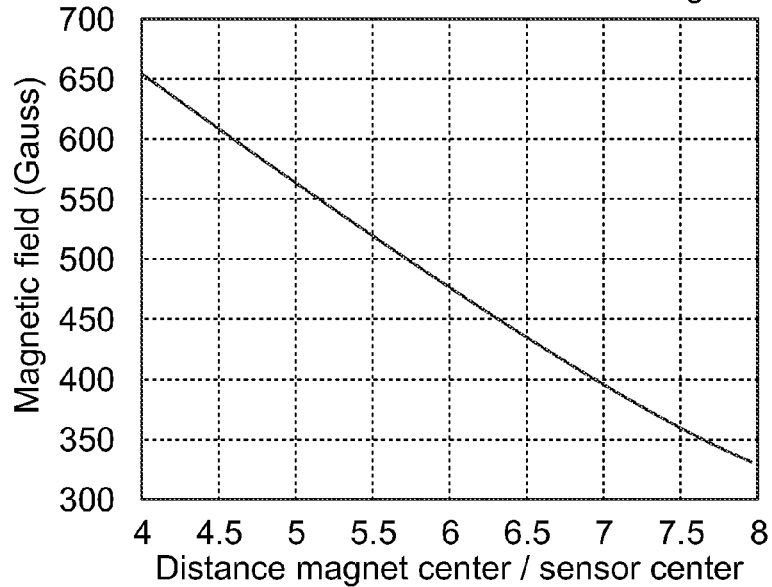
FIG. 39 is a plot of magnetic field intensity measured by the sensor.

In an exemplary embodiment, a minimum signal/noise ration of $(B_{magnet})_{min}/(B_{coil})_{max}=45$ and a sensitivity ratio $\Delta B_{magnet}/\Delta z \sim 75\text{-}100$ Gauss/mm (depending on the position) ~220 mV/mm have been determined with z being the position of the magnet (considering a maximum distance of 8 mm and a maximum current of 0.3 A through the coil). Performances and coil perturbation have been measured with the sensor being at the side location, as shown in FIGS. 38, 39.

The chosen location permits to optimize the signal/noise ratio, not to suppress completely the magnetic perturbation of the coils. In order to achieve this accurately, a noise suppression system has been configured, based on the separation of coil and magnet components of the magnetic field, thanks to the use of pulses.

When a step voltage is applied to the coils at $t=t_0$, the system response is the following:

$$B_{sensor}(t)=B_{sensor}(t_0)+\Delta B_{coil}(t-t_0)+\Delta B_{magnet\_displacement}(t-t_0)$$

Where $\Delta B_{coil}+\Delta B_{magnet\_displacement}$ is the total change $\Delta B_{sensor}$ of the radial magnetic field measured by the sensor, after the step voltage is applied. $\Delta B_{coil}$ is the magnetic perturbation due to the coil, which is the contribution of the coils to this change (because the coils create a magnetic field); $\Delta B_{magnet\_displacement}$ is contribution of the magnets to this change (because the magnets move, and hence the distance to the sensor changes and so the magnetic field measured by the sensor changes).

These two terms have different intrinsic response times. $\Delta B_{coil}$ is proportional to the current I flowing in the coil and has thus an electrical response time $\tau_I = L/R$. $\Delta B_{magnet\_displacement}$ is due to the displacement of the magnets. Once the magnetic field is applied, the magnets accelerate until they reach a nearly constant speed. The time needed to reach this constant speed will be a mechanical response time $\tau_M$. In the present example, $\tau_I \ll \tau_M$. This means that when a voltage step is applied, $\Delta B_{coil}$ has reached a final value while $\Delta B_{magnet\_displacement}$ is still negligible. Therefore, we have:

$$\Delta B_{coil}(I) = \left[\frac{B_{sensor}(t_0 + t_1) - B_{sensor}(t_0)}{I(t_0 + t_1)}\right] * I \quad (19)$$

With $t_1 \gg \tau_I$ and $t_1 \ll \tau_M$. In the present case, $t_1 \sim 0.2$ ms is the optimum value.

Formula (19) shows that it is possible to derive independently the perturbation of the coil even while a magnet is inside the pump, thanks to applied pulse signals, by measuring the response at a time $t_1$, before the magnet has time to move.

Figure 40:
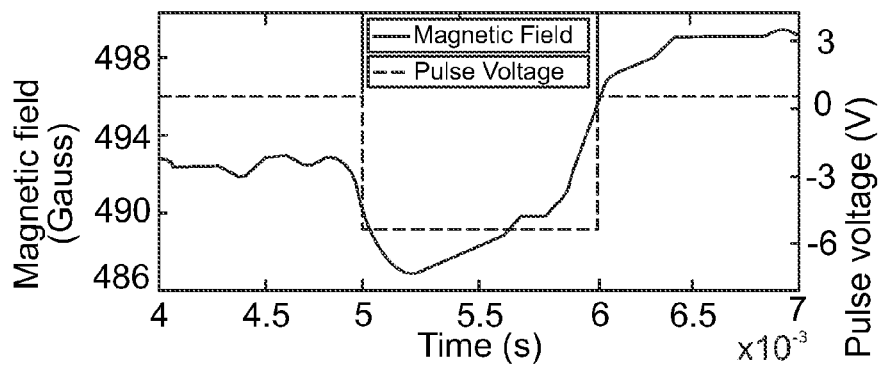
FIG. 40 is a plot of sensor responses to voltage pulses.
Figure 40:
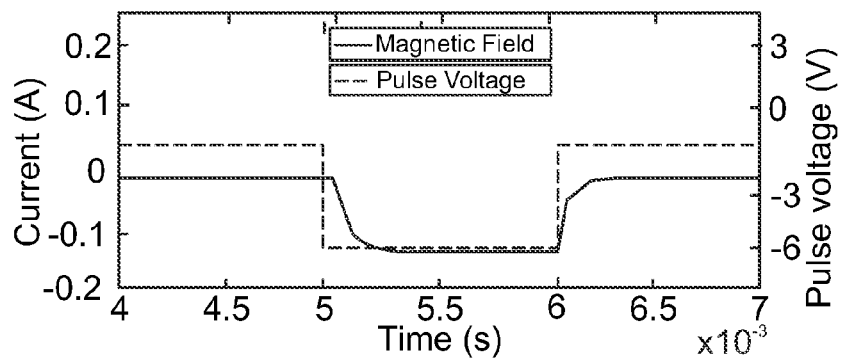
Figure 41:
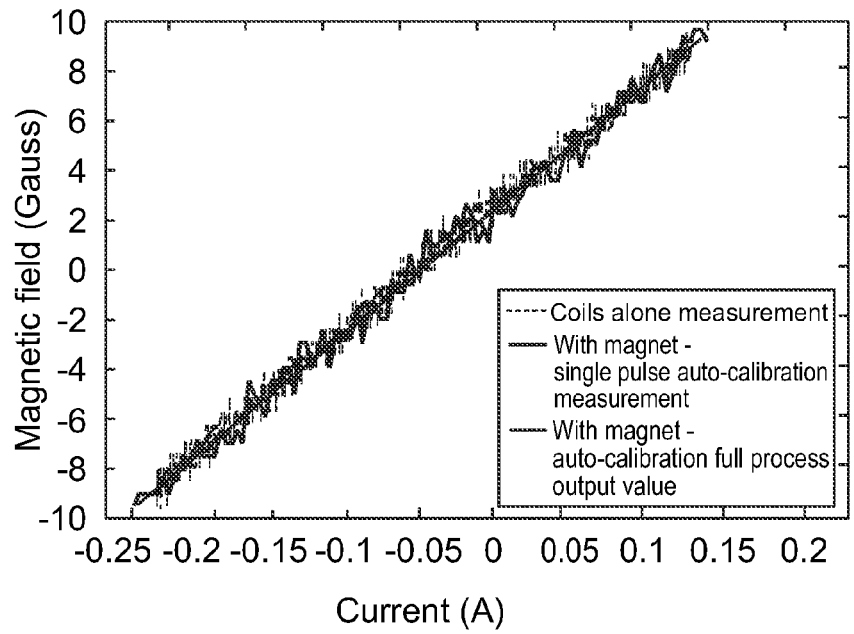
FIG. 41 is a plot of perturbation measurement.

Based on this principle, the sensor response to voltage pulses (see FIG. 40) was measured and used to calculate the magnetic perturbation of the coil $\Delta B_{coil}(I)$ (see FIG. 41). The sensor response was compared to its actual value, which was measured directly from the coils alone; by removing the magnets from the pump (see FIG. K). Note that the measurement is noisy, due to the intrinsic sensor noise level and to the limited CAN conversion precision at this level of precision (1 Gauss=½₀₀₀ of the sensor measurement range).

The following protocol leads to reproducible, accurate values (see FIG. 41): 5 pulses +10 V, 1 ms duration are applied, one every 10 ms; 5 pulses −10 V, 1 ms duration are applied, one every 10 ms; The current and magnetic fields are measured. The average coil perturbation factor of the pulses is calculated according to the equation $$A_{coil} = \left\langle \frac{\Delta B_{coil}(I)}{I} \right\rangle$$

After $A_{coil}$ is calculated, $A_{coil}$ is used in real-time during the measurements, wherein:

$B = B_{measured} - A_{coil} * I$

The proposed perturbation measurement method is both accurate and quick, and can be used in situ with a magnet already inside the micropump. This is the first part of the auto-calibration process of the sensory system. The second part is described as follows.

Once the coil perturbation is suppressed, the measured signal corresponds to the magnetic field $Br_{magnet}$ created by the magnets at the sensor level. The measured signal is not a linear function of the magnet position. Therefore, a position determination algorithm is used, which transforms the sensor signal into the magnets position.

A magnet of magnetization M creates at a point r′ exterior to the magnet a magnetic field:

$$B(r') = -\frac{\mu_0}{4\pi}(M.grad)\left(\int_{V_{magnet}} \frac{(r-r')}{\|r-r'\|^3} dV\right) \quad (20)$$

Where r is the coordinates of the elementary volume dV in the volume $V_{magnet}$ of the magnet, used in the volumetric integration in (20).

In the present example, the magnets have a axisymmetric geometry, such that for each magnet:

$$B_r(z_{bottom}) = \frac{B_{rem}}{4\pi} \frac{\partial}{\partial z_s}$$
$$\int_{z=z_{bottom}}^{z_{bottom}+h} \int_{r=0}^{R} \int_{\theta=0}^{2\pi} \frac{(r_s - r\cos\theta)}{[(r\sin\theta)^2 + (r_s - r\cos\theta)^2 + (z_s - z)^2]^{\frac{3}{2}}} r\,d\theta\,dr\,dz$$

$$B_z(z_{bottom}) = \frac{B_{rem}}{4\pi} \frac{\partial}{\partial z_s}$$
$$\int_{z=z_{bottom}}^{z_{bottom}+h} \int_{r=0}^{R} \int_{\theta=0}^{2\pi} \frac{(z_s - z)}{[(r\sin\theta)^2 + (r_s - r\cos\theta)^2 + (z_s - z)^2]^{\frac{3}{2}}} r\,d\theta\,dr\,dz$$

Where the reference (0,0,0) is the center of the pump chamber. $B_{rem}$ is the remnant magnetic field inside the magnet. $(r_s, z_s)$ are the coordinates of the center of the sensor; R is the radius of the magnet, h is the thickness of the magnet, and $z_{bottom}$ is the coordinates of the bottom of the magnet.

Once the effects of the coil are suppressed, the magnetic field measured by the sensor is the superposition of the magnetic field of both magnets.

$$B_{sensor} = B_r\left(z_m + \frac{h_m}{2}\right) + B_r\left(z_m - h - \frac{h_m}{2}\right) \quad (21)$$

Formula (21) cannot be used in itself to determine the position $z_m$ of the center of magnets (and hence the position of the membrane), as its integrations do not give any analytic solution, so that it is impossible to obtain the inverse function of (21). A lookup table of (21) and the corresponding reverse lookup table have to be created.

The real system is not ideal and the parameters of the equation can only be known with a limited precision. Therefore, the simulated values of $z_m$ as a function of $B_{measured}$ will be different from the real values. However, it is possible to reduce strongly the difference between real and simulated values by using the following formula:

$$B_{simulated\_corrected}(z) = B_{simulated}(z) * \left[\frac{B_{max\_measured}}{B_{max\_simulated}} + \right. \quad (22)$$
$$\left. \left(\frac{z - z_{Bmax}}{z_{Bminx} - z_{Bmax}}\right) * \left(\frac{B_{min\_measured}}{B_{min\_simulated}} - \frac{B_{max\_measured}}{B_{max\_simulated}}\right)\right]$$

Formula (22) enables to use corrected simulated values which are very close from the real values to determine accurately the position of the magnet, given that we know the real $Br_{magnet}$ in two cases: for $z_{Bmax}$ and $z_{Bmin}$. $z_{Bmax}$ and $z_{Bmin}$ are easy to obtain, as they are the position of the magnet when it hits the lower wall ($z_{Bmax}$) and upper wall ($z_{Bmin}$).

Following this principle, the position of the magnet can be obtained through the following protocol:

(a) According to the dimension of the pump, the position of the sensor and the size and material of the magnets, a simulation is done offline with the formula (21);

(b) A lookup table is generated and recorded in the microcontroller memory during the burning of the program;

(c) Each time the pump is on again or a new pump part is inserted, the maximum and minimum positions are searched and the corresponding magnetic fields are measured;

(d) Formula (22) is used to modify the lookup table and then create the reverse lookup table which gives $z_m$ as a function of $B_{measured}$; and (e) $z_m$ is obtained from $B_{measured}$ in real time by using a linear regression on the reverse lookup table;

Wherein steps c and d are done automatically and do not exceed 1 s.

Figure 42:
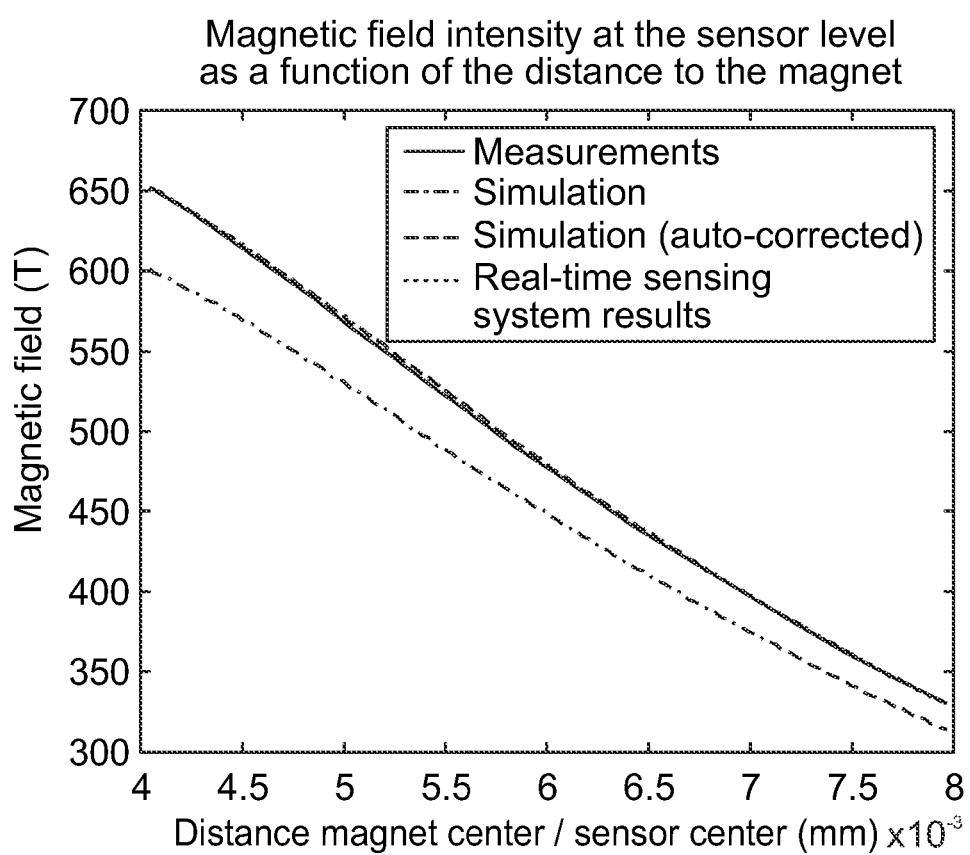
FIG. 42 is a plot of measured magnetic field as a function of magnet position.

The magnetic field created by the magnets is measured by the sensor as a function of the magnet position (see FIG. 42). In FIG. 42, the magnetic field is plotted as a function of: (i) the simulated magnetic field; (ii) the corrected simulated values according to formula (22); and (iii) the real-time linear regression on the lookup table that was created with the previously described protocol.

The maximum error between the real values and the calculated reverse lookup table values has been measured: $Error_{max}$=0.03 mm=0.75% of the total range of the magnets inside the pump, i.e. with a precision of 0.75% of the chamber volume.

Figure 43:
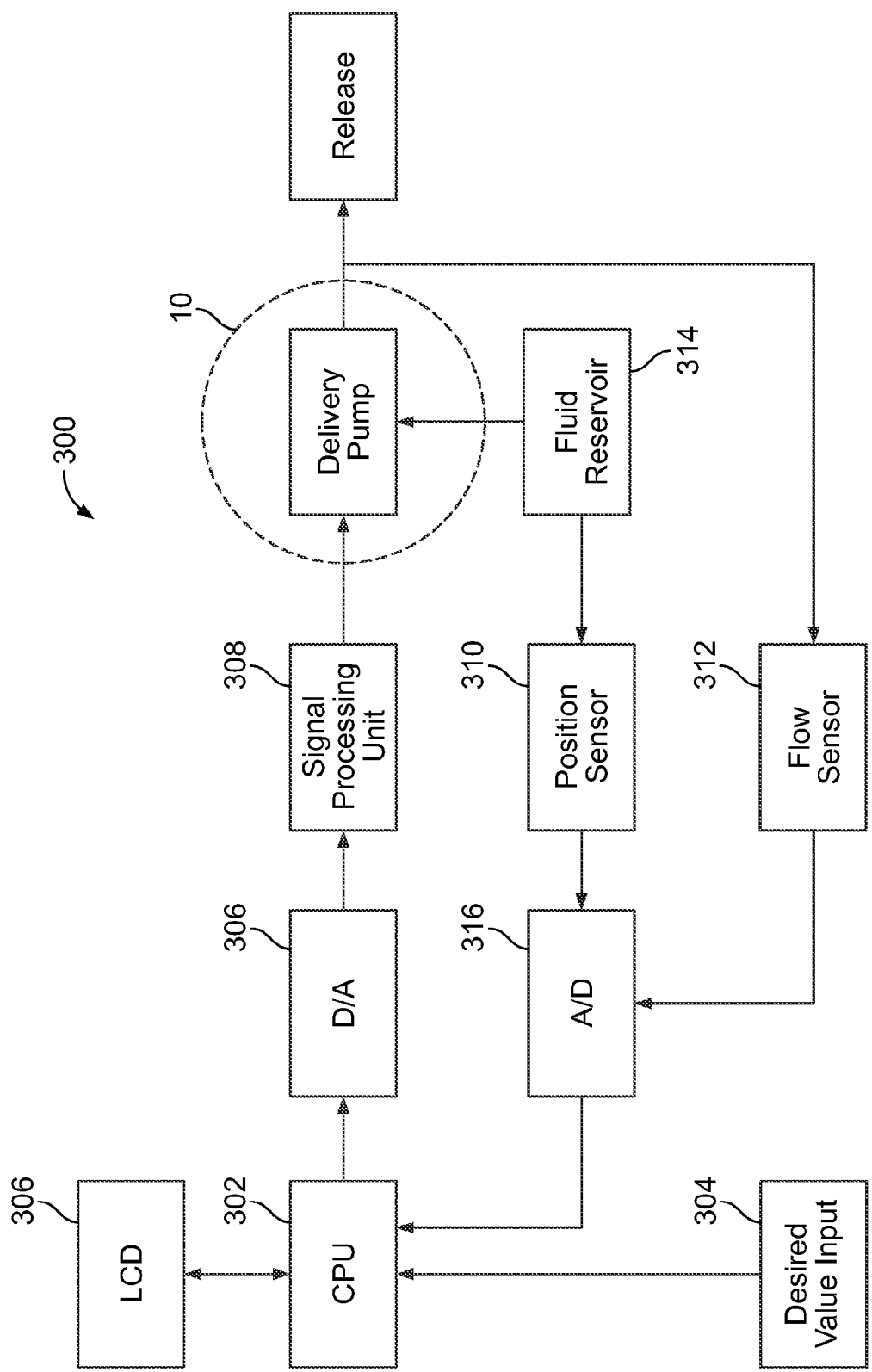
FIG. 43 is a schematic representation of a control system embodiment of the present disclosure.
Figure 44:
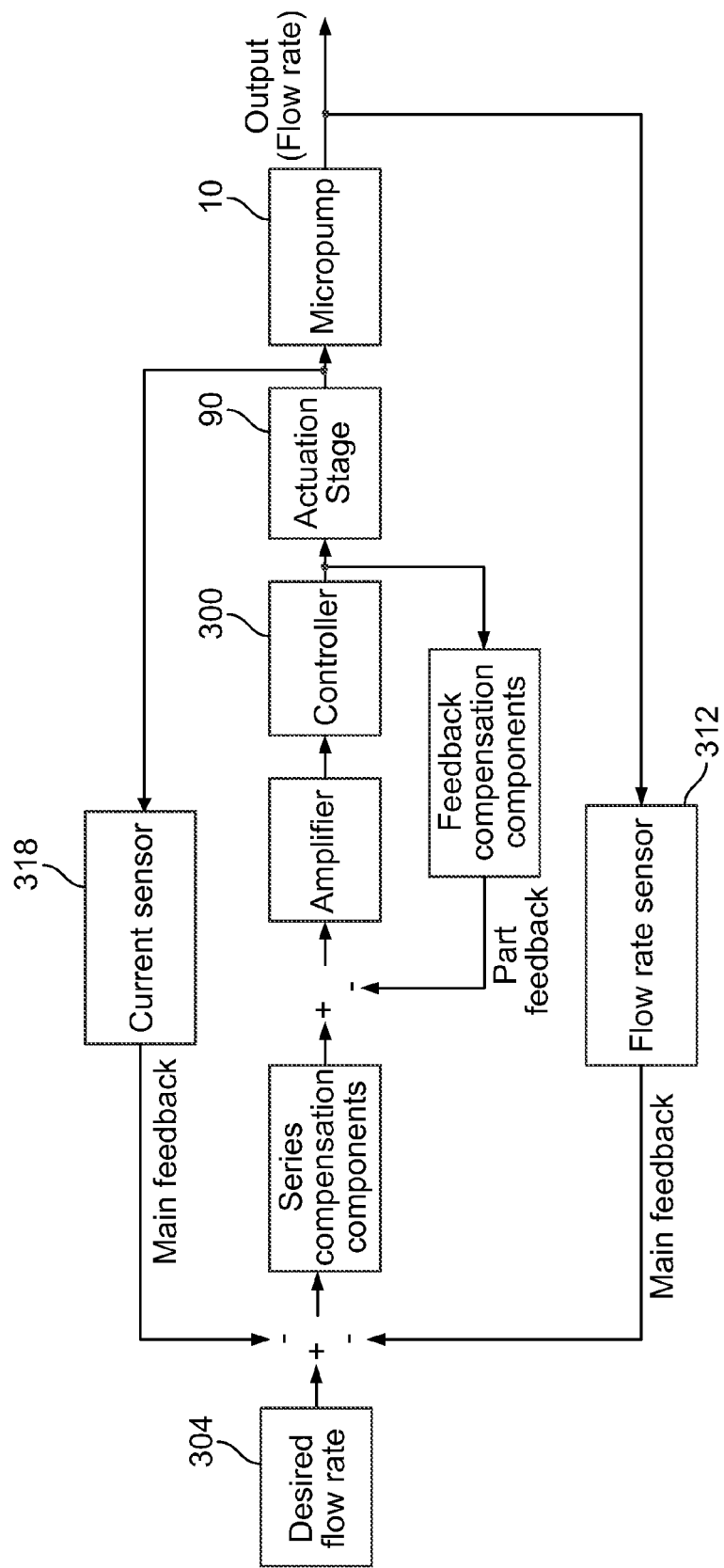
FIG. 44 is a schematic representation of a feedback loop of the present disclosure.

A control system 300 is included in an exemplary embodiment of the present disclosure. Referring to FIG. 43, control system 300 includes a central processing unit (CPU) 302 configured to receive user input 304. A display 306, such as a liquid crystal display (LCD) is provided to allow the user to see various parameter values, such as flow rate, volume, power, battery charge, etc. The CPU 302 provides an actuation signal which is passed through a digital to analog (D/A) 306 converter and a signal processing unit 308. In addition to the Hall effect position sensor 310 adjacent to magnetic coil, as described previously, an embodiment of the micropump of the present disclosure may also include flow sensors 312 on the outlet of the micropump, and a volume sensor 314 on the fluid reservoir. The values are passed through an analog to digital (A/D) 316 controller before being provided to the CPU 302. The values obtained from these sensors may be compared to provide additional feedback to the controller to optimize flow rate and/or to provide a warning or alarm condition if these parameters exceed predetermined values, as shown in FIG. 44.

In an exemplary embodiment of the present disclosure, two different PID controllers were used: (i) the first PID includes a setpoint for the current I, and the output voltage U; (ii) a second PID includes a setpoint for the position of magnet x, and the output of the current I. The sensing system has a physical input of the signal from current sensor 318 and transforms it into the magnet position x after noise suppression (as discussed previously).

Figure 45:
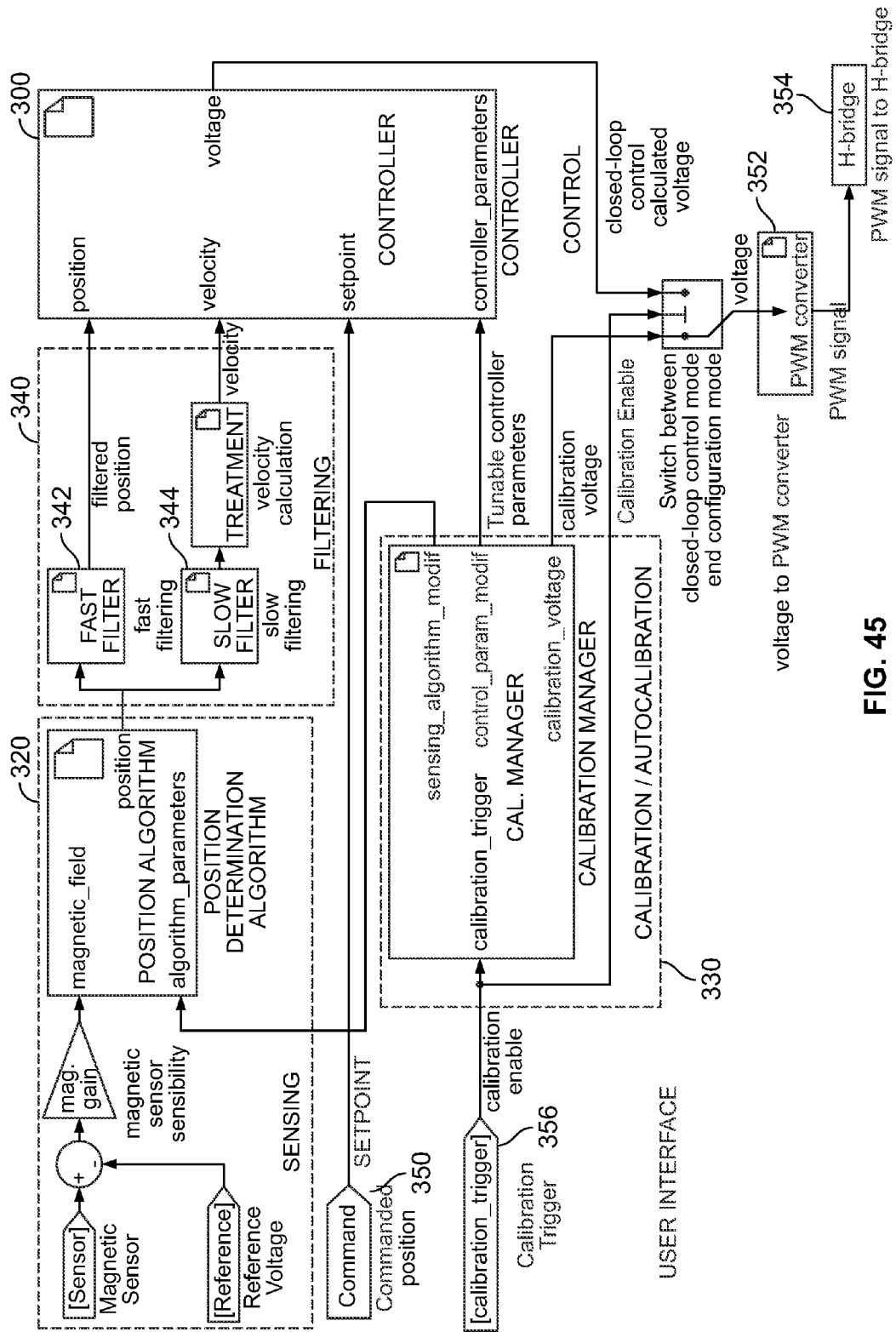
FIG. 45 is a detailed schematic representation of the control system of FIG. 43.

An exemplary embodiment of control system architecture is shown in FIG. 45. Controller 300 may receive input from a sensing module 320 and a calibration manager 330 for operation in a sensing mode and a calibration mode. Further, the signal provided by the sensing module 320 may pass through a filter module 340 before being processed by controller 300.

Figure 47:
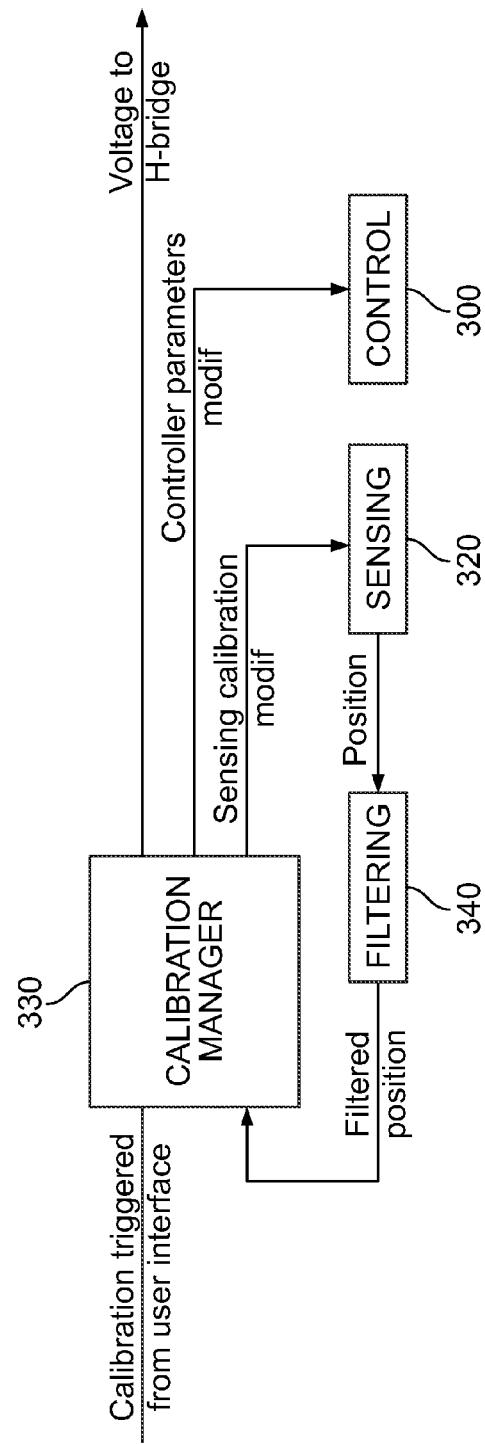
FIG. 47 is a flow chart of operation of the control system of the present disclosure in calibration mode.

When operated in calibration mode a calibration trigger 356 or requirement is provided by a user interface. The calibration manager 330 takes control of the position of the magnets on the flexible membrane by sending a calibration signal to the PWM converter 352. The position of the magnet is recorded and the controller parameters are modified. Operation is then returned to controller with the updated parameters and calibration. A simplified flow chart of operation in calibration mode is shown in FIG. 47.

Figure 46:
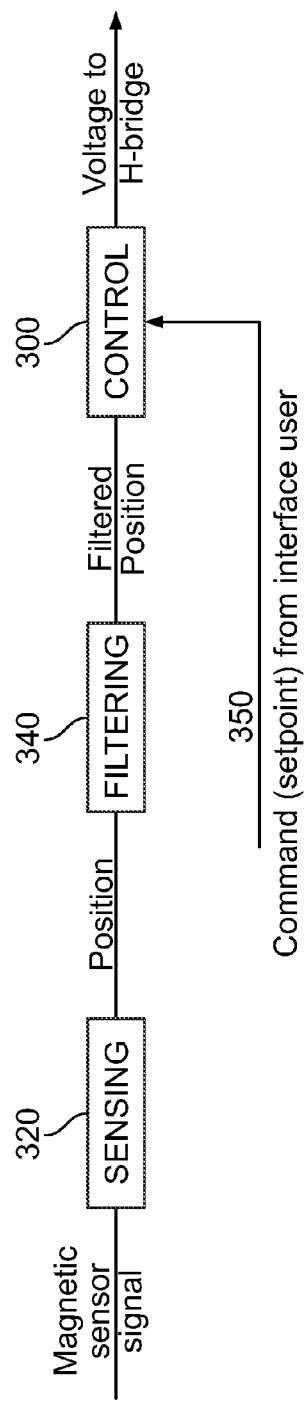
FIG. 46 is a flow chart of operation of the control system of the present disclosure in sensing mode.

When operated in sensing mode, user interface 350 provides the required flow rate requirements, which are then transformed by controller 300 into displacement commands for the magnet disposed on the flexible membrane. These commands are then used as a set point for controller 300. Controller compares in real time the set point of the magnet's position with actual position. Based on this comparison, controller 300 sends a voltage signal to pulse width modulation (PWM) converter 352. PWM converter 352 then transforms the voltage signal from the controller into a PWM signal, which is then supplied to an H-bridge circuit 354 that controls the current flowing to the actuator coils. A simplified flow chart of operation in sensing mode is shown in FIG. 46.

Because the exemplary embodiment of the micropump of the present disclosure uses a Hall effect sensor to detect the position of the flexible membrane through the strength of the magnetic field produced by the magnets disposed on the membrane, the signals need to be transformed into a position value. An exemplary embodiment employs a look-up table based upon an electromagnetic field model to provide the position of the magnets as a function of magnetic field strength. The electromagnetic field model is calculated prior to programming the controller based on parameters such as component dimensions and materials used, as discussed previously. Since the results of these calculations are approximations of the physical embodiment, calibration enables the system to sense the actual position/magnetic field relationship with a precision of approximately 0.03 mm.

The feedback signals provided by the sensing module 320 contain noise, due to the use of the PWM driver circuit and the properties of the magnetic field. Therefore, filter module 340 is used to suppress noise in the signal. Filter module includes two filters: a fast filter 342 and a slow filter 344. Fast filter 342 is less precise, but is adapted for operations which are less sensitive to noise oscillations, such as integrations. Slow filter 344 is more precise; however, the increased precision also increases the delay time. Slow filter is suitable for measuring the velocity of the magnet, taking into account the delay.

Figure 48:
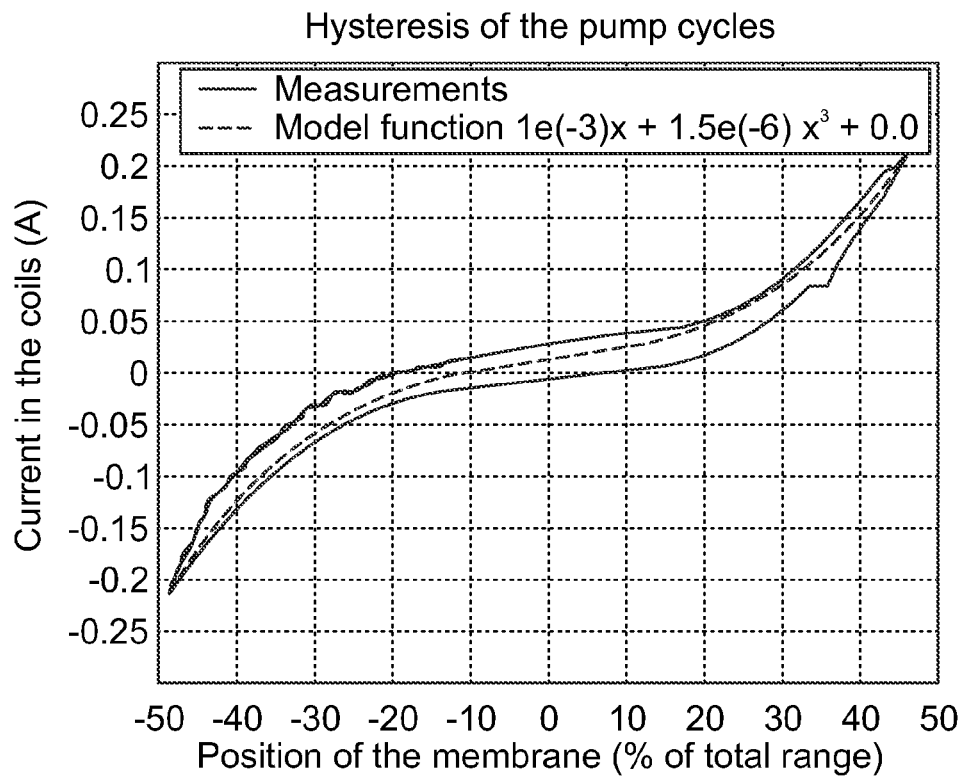
FIG. 48 is a hysteresis plot for a micropump embodiment of the present disclosure.
Figure 49:
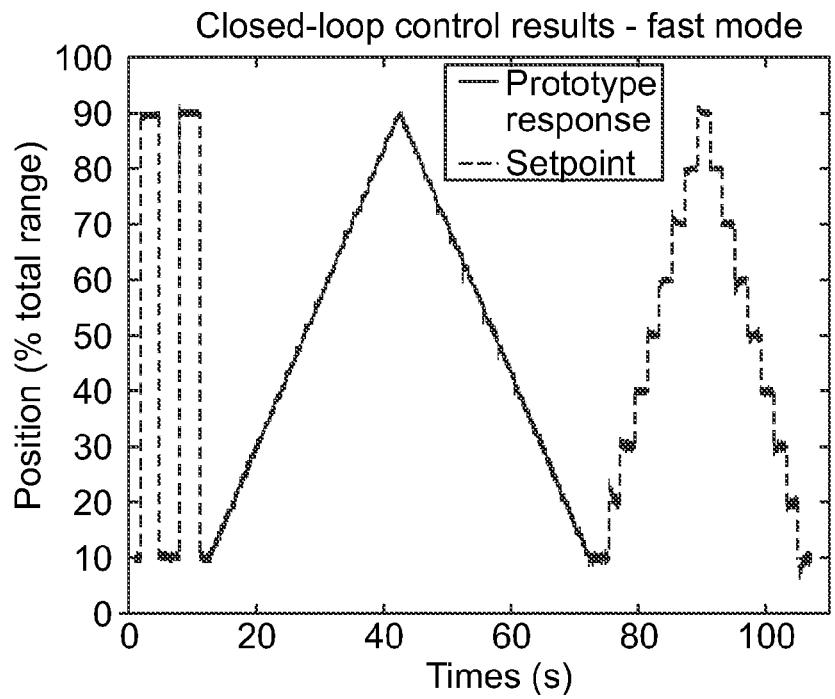
FIG. 49 is a plot of position and set point in a closed-loop control system of the present disclosure.

The system has a clear mechanical hysteresis; moreover, the current—and hence the magnetic field—is neither a linear nor a univocal function of the voltage, due to the heating of the coils, as shown in FIG. 48. This prevents to control it with an open loop signal. Despite the hysteresis, which prevents usually from obtaining much better results than the hysteresis amplitude, the prototype response is both quick-time response for high amplitude setpoints change: and accurate–static error=0; maximal overshoot error=2%, as shown in FIG. 49.

Figure 50:
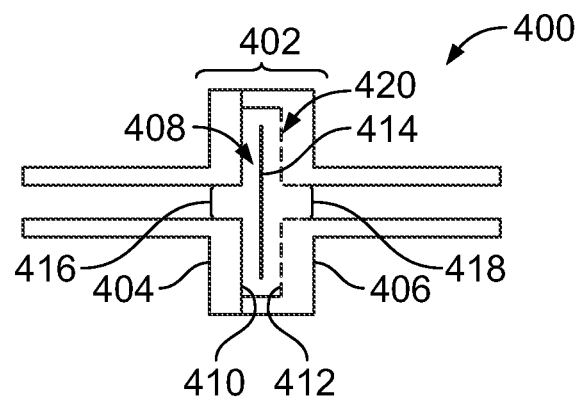
FIGS. 50-52 depict check valves that may be used with the micropump of the present disclosure.
Figure 51:
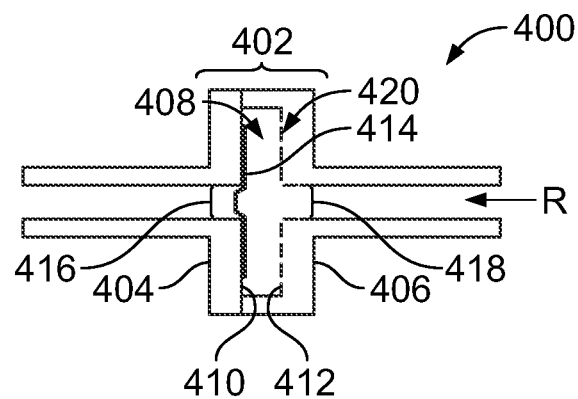
Figure 52:
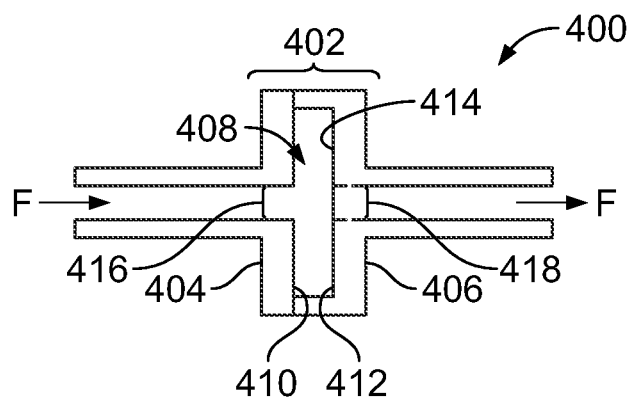

In addition to the valveless micropump embodiment of the present disclosure, described above, an alternative embodiment may employ check valves to provide a one-way fluid flow path. Referring to FIGS. 50-52, an exemplary embodiment of a check valve 400 used with the micropump of the present disclosure, includes a valve body 402, which may be formed from a pair of body components 404, 406 bonded together. Body components 404, 406 define a chamber 408 having a par of substantially flat surfaces 410, 412 disposed apart and facing each other that act as seats for a membrane 414 disposed within chamber 408. Check valve 400 also includes an inlet port 416, and an outlet port 418 in fluid communication with chamber 408. Membrane 414 is configured to float within chamber 408, and in an exemplary embodiment is approximately 20% smaller than chamber 408. Seat 410, positioned adjacent inlet port 416 is solid.

Seat 412 positioned adjacent to outlet port 418 includes a number of apertures 420 allowing fluid to pass through. In an exemplary embodiment, such apertures 420 have been machined into seat 412 in a rosette pattern, however, any pattern allowing flow through valve 400 while membrane 414 is seated against seat 412 is acceptable.

Referring now to FIGS. 51 and 52, at any point where there exists a fluid pressure at the outlet port 418 that is greater than the fluid pressure at the inlet port 416, reverse fluid flow conditions will develop as shown in FIG. 51 by arrow R. This reverse flow acts to sweep membrane 414 towards inlet seat 410. After membrane 414 is seated against inlet seat 410, membrane 414 covers inlet port 416 preventing further reverse flow.

At any point where there exists fluid pressure at the inlet port 416 that is greater than the fluid pressure at the outlet port 418, forward fluid flow conditions will develop as shown by arrows F in FIG. 52. This forward flow sweeps membrane 414 towards outlet seat 412. Because outlet seat 412 contains apertures 420, fluid is allowed to flow around membrane 414 passing through these apertures 420, thereby allowing fluid to flow through outlet port 418 in the forward fluid flow F direction.

Figure 53:
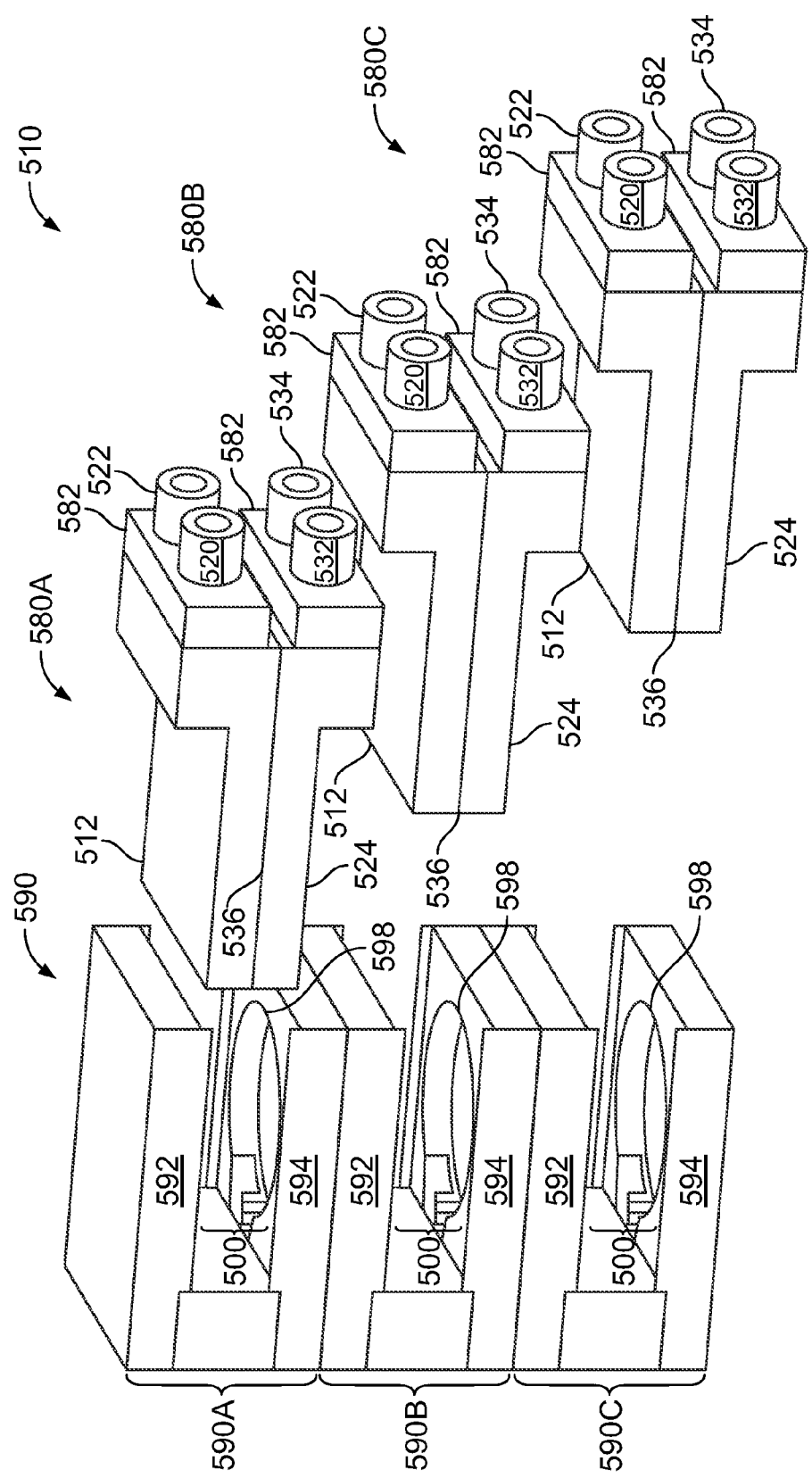
FIG. 53 is an exemplary embodiment of a multichamber micropump of the present disclosure.

Referring now to FIG. 53, another embodiment of the present disclosure includes a multichamber micropump 510. The multichamber micropump 510 may be configured as a number of pump cartridges 580A, 580B, 580C, configured for insertion into a driver 590. Although three pump cartridges are shown, it should be apparent that more or fewer cartridges are within the scope of the present disclosure and may vary depending on the application of the micropump of the present disclosure. Each of the pump cartridges 580A, 580B, and 580C is identical to the others, and therefore pump cartridge 580A will be described as the exemplary embodiment.

Pump cartridge 580A includes a first pump body 512, a second pump body 524, and a flexible membrane 536 disposed therebetween. Pump cartridge may optionally include a check valve manifold 582. Alternatively, pump cartridge 580A may be of a valveless design as disclosed herein. Pump cartridge 580A also includes inlets 520, 532 and outlets 522, 534. Tubing may then be connected to inlets 520, 532 and outlets 522, 534 for fluid delivery.

Driver 590 includes a number of receiver modules 590A, 590B, 590C, corresponding to the number of pump cartridges 580A, 580B, 580C. As an exemplary embodiment, receiver module 590A includes a first support 592 and a second support 594. The first and second supports 592, 594 each include a recess 598 configured to receive a solenoid or activation coil. Each receiver module 590A, 590B, 590C, defines a receptacle 500 configured to receive pump cartridges 580A, 580B, 580C. Receiver modules may be configured in a stacked arrangement as shown in FIG. 53, or may be arranged in other configurations such as back-to-back, side-by-side, or combinations thereof, depending on the desired application.

The foregoing is considered as illustrative only of the principles of the claimed invention. Further, since numerous modifications and changes will readily occur to those skilled in the art, it is not desired to limit the claimed invention to the exact construction and operation shown and described, and accordingly, all suitable modifications and equivalents may be resorted to, falling within the scope of the claimed invention.

The invention claimed is:

1. A micropump for delivering a fluid, the micropump comprising:
   a pump assembly including
     a first pump body defining a first fluid body flow path, the first pump body including
       a first chamber, the first chamber including a first chamber wall and a first side wall,
       a first inlet and a first outlet, wherein the first inlet and first outlet are in fluid communication with the first chamber,
     a second pump body defining a second fluid body flow path, the second pump body including
       a second chamber, the second chamber including a second chamber wall and a second side wall,
       a second inlet and a second outlet, wherein the second inlet and the second outlet are in fluid communication with the second chamber, and
     a flexible membrane disposed between the first chamber and the second chamber;
   a first magnet affixed to the membrane; and
   an actuator assembly configured to cooperate with the pump assembly, the actuator assembly including
     a driver magnetically coupled to the membrane, where the driver comprises a magnetic coil and
     a sensor configured to detect the position of the first magnet affixed to the membrane, where the sensor is located adjacent to the magnetic coil at a location where the magnetic flux density of the magnetic coil is negligible compared to the magnetic flux density of the first magnet,
   wherein the driver applies a magnetic force to the first magnet affixed to the membrane, causing the membrane to deflect, and wherein such deflection of the membrane results in a change of pressure within the first chamber and the second chamber thereby resulting in fluid flow, and
   wherein the pump assembly is configured to direct the fluid flow in a predetermined direction without a valve.

2. The micropump of claim 1 wherein the first inlet further includes a first inlet passage, the first inlet passage including
   a first inlet throat having a first inlet throat width and a first inlet end having a first inlet end width,
   wherein the first inlet passage is configured such that fluid flows in a direction from the first inlet throat to the first inlet end, and
   wherein the first inlet end is disposed in the first side wall, and wherein the first inlet throat width is less than the first inlet end width.

3. The micropump of claim 2 wherein the first outlet further includes a first outlet passage, the first outlet passage including
   a first outlet throat having a first outlet throat width and a first outlet end having a first outlet end width,
   wherein the first outlet passage is configured such that fluid flows in a direction from the first outlet throat to the first outlet end, and
   wherein the first outlet throat is disposed in the first side wall, and wherein the first outlet throat width is less than the first outlet end width.

4. The micropump of claim 3 wherein the first inlet passage and the first outlet passage are configured to allow fluid flow through the first chamber in the direction from the first inlet to the first outlet.

5. The micropump of claim 1 further including:
a first inlet passage including
   a first inlet throat having a first inlet throat width and a first inlet end having a first inlet end width,
   wherein the first inlet passage is configured such that fluid flows in a direction from the first inlet throat to the first inlet end, and
   wherein the first inlet end is disposed in the first side wall, and wherein the first inlet throat width is less than the first inlet end width;
a first outlet passage including
   a first outlet throat having a first outlet throat width and a first outlet end having a first outlet end width,
   wherein the first outlet passage is configured such that fluid flows in a direction from the first outlet throat to the first outlet end, and
   wherein the first outlet throat is disposed in the first side wall, and wherein the first outlet throat width is less than the first outlet end width;
a second inlet passage including
   a second inlet throat having a second inlet throat width and a second inlet end having a second inlet end width,
   wherein the second inlet passage is configured such that fluid flows in a direction from the second inlet throat to the second inlet end, and
   wherein the second inlet end is disposed in the second side wall, and wherein the second inlet throat width is less than the second inlet end width;
a second outlet passage including
   a second outlet throat having a second outlet throat width and a second outlet end having a second outlet end width,
   wherein the second outlet passage is configured such that fluid flows in a direction from the second outlet throat to the second outlet end, and
   wherein the second outlet throat is disposed in the second side wall, and wherein the second outlet throat width is less than the first outlet end width.

6. The micropump of claim 1 further comprising a second magnet disposed upon the membrane, wherein the first magnet is positioned adjacent to the first chamber and the second magnet is positioned adjacent the second chamber.

7. The micropump of claim 1 comprising a plurality of magnets, the plurality of magnets being disposed on the membrane adjacent to either of the first chamber and the second chamber.

8. The micropump of claim 1 wherein the first magnet is a neodymium-iron-boron rare earth magnet.

9. The micropump of claim 6 wherein the second magnet is a neodymium-iron-boron rare earth magnet.

10. The micropump of claim 1 wherein the flexible membrane is constructed of a soft polymer material mixed with a magnetic material.

11. The micropump of claim 10 wherein the soft polymer material is polydimethylsiloxane.

12. The micropump of claim 1 wherein the flexible membrane is configured for adjustable tensioning, allowing the flexibility of the membrane to be changed in relation to the magnetic force applied to the membrane by the driver.

13. The micropump of claim 1 wherein the sensor is a Hall effect sensor.

14. The micropump of claim 1 wherein the driver further includes a feedback control system configured to control displacement of the membrane by sensing the position of the magnet attached to the membrane, comparing the position to a predetermined set point, and adjusting the magnetic force applied to the membrane.

15. A micropump assembly for delivering a fluid from a fluid reservoir, the micropump assembly comprising:
a pump cartridge including
   a first pump body defining
      a first chamber, the first chamber including a first chamber wall and a first side wall,
      a first inlet and a first outlet, wherein the first inlet and first outlet are in fluid communication with the first chamber,
   a second pump housing defining
      a second chamber, the second chamber including a second chamber wall and a second side wall,
      a second inlet and a second outlet, wherein the second inlet and the second outlet are in fluid communication with the second chamber, and
   a flexible membrane disposed between the first chamber and the second chamber,
   wherein the pump cartridge is configured to allow fluid communication from the fluid reservoir to at least one of the first chamber and the second chamber; and
a housing enclosing
   an actuator assembly configured to cooperate with the micropump cartridge, the actuator assembly including
      a driver magnetically coupled to the membrane, and
      a first sensor configured to detect the position of the membrane,
   wherein the driver applies a magnetic force to the membrane, causing the membrane to deflect, and wherein such deflection of the membrane results in a change of pressure within the first chamber and the second chamber thereby resulting in fluid flow,
   a controller coupled to the driver and configured to control the position of the membrane by receiving input from the first sensor and adjusting the magnetic force applied by the driver, and
   a power supply configured to energize the driver and the controller,
wherein the housing is configured such that the micropump cartridge may be inserted into and retained within the actuator assembly.

16. The micropump assembly of claim 15 wherein the micropump cartridge is configured for a single use.

17. The micropump assembly of claim 16 wherein the fluid reservoir is attached to the micropump cartridge.

18. The micropump assembly of claim 16 wherein the fluid reservoir is contained within the housing and is configured for coupling with the micropump cartridge upon insertion of the micropump cartridge into the housing.

19. The micropump assembly of claim 15 wherein the controller is configured to receive a feedback signal from the first sensor, and wherein the controller is configured to compare the position of the magnet attached to the membrane to a predetermined set point, and wherein the controller is configured to adjust the magnetic force applied to the membrane in response to the feedback signal.

20. The micropump assembly of claim 19 wherein the controller is a proportional-integral-derivative type controller.

21. The micropump assembly of claim 15 further including a second sensor configured to detect a volume of fluid within the fluid reservoir, and wherein the controller is configured to receive input from the second sensor such that the controller is able to calculate and predict fluid flow.

22. The micropump assembly of claim 15 wherein the controller is configured to calculate the volume of fluid delivered based on the feedback signal from the first sensor.

23. The micropump assembly of claim 22 wherein the controller is configured to compare the volume of fluid delivered based on the feedback signal from the first sensor with the volume input from a second sensor, and wherein the controller is configured to provide an output signal if the compared volumes are outside of a predetermined range.

24. The micropump assembly of claim 23 wherein the output signal is at least one of an alarm and shutting down.

25. A method of fabricating a micropump, the method comprising the steps of:
fabricating a flexible membrane from a polymer material including the steps of
spin coating a first polymer layer on a silicon wafer and allowing the first polymer layer to cure,
placing magnetic material on the first polymer layer,
applying a second polymer layer around the magnetic material and allowing the second polymer layer to cure, and
applying a third polymer layer and allowing the third polymer layer to cure;
fabricating a rigid pump body by pouring liquid polymer material into a mold configured to form a fluid chamber, an inlet channel, and an outlet channel, and allowing the liquid polymer to cure;
aligning the flexible membrane with the rigid pump body; and
bonding the flexible polymer membrane to the rigid pump body.

26. The method of claim 25 wherein the first polymer layer is spin coated to a thickness of approximately 0.15 mm.

27. The method of claim 26 wherein the first polymer layer is allowed to cure at 75 degrees Celsius for 2 hours.

28. The method of claim 25 wherein the second polymer layer is applied to a thickness of approximately 0.5 mm.

29. The method of claim 26 wherein the second polymer layer is allowed to cure at 100 degrees Celsius for 30 minutes.

30. The method of claim 25 wherein the third polymer layer is applied to a thickness of approximately 0.15 mm.

31. The method of claim 30 wherein the third polymer layer is allowed to cure at 75 degrees Celsius for 2 hours.

32. The method of claim 25 wherein the mold for the rigid pump body is formed from an epoxy-based negative photoresist material.

33. The method of claim 32 wherein the photoresist material is SU-8.

34. The method of claim 25 wherein bonding of the flexible polymer layer to the rigid pump body is performed using an adhesive.

35. The method of claim 25 wherein bonding of the flexible polymer membrane is performed using an oxygen plasma method including the step of curing a film of polymer disposed between the flexible membrane and the molded pump body at 100 degrees Celsius for 20 minutes.

36. The method of claim 25 wherein bonding of the flexible polymer membrane is performed using an oxygen plasma method including the step of curing a film of uncured polymer between the flexible membrane and the molded pump body by applying microwaves in an atmosphere of 10% oxygen for 10 seconds.

37. The method of claim 25 wherein the polymer material is selected from the group consisting of parylene, polyimide, SU-8, and polydimethylsiloxane.

38. The method of claim 25 wherein the flexible membrane is fabricated from a mixture of 10 parts polydimethylsiloxane and 1 part curing agent.

39. The method of claim 25 wherein the rigid pump body is fabricated from a mixture of 5 parts polydimethylsiloxane and 1 part curing agent.

40. A micropump for delivering a fluid, the micropump comprising:
a pump assembly including
a first pump body defining
a first chamber, the first chamber including a first chamber wall and a first side wall,
a first inlet and a first outlet, wherein the first inlet and first outlet are in fluid communication with the first chamber, and
a first flexible membrane disposed over the first chamber opposite the first chamber wall,
a second pump body defining
a second chamber, the second chamber including a second chamber wall and a second side wall,
a second inlet and a second outlet, wherein the second inlet and the second outlet are in fluid communication with the second chamber, and
a second flexible membrane disposed over the second chamber opposite the second chamber wall;
at least a third pump body disposed between the first pump body and the second pump body, the third pump body defining
a third chamber including a third side wall,
third inlet and a third outlet, wherein the third inlet and the third outlet are in fluid communication with the third chamber,
wherein the at least third chamber is adjacent the first membrane and the second membrane; and
an actuator assembly configured to cooperate with the pump assembly, the actuator assembly including
a driver magnetically coupled to the first membrane and the second membrane, and
at least one sensor configured to detect the position of the first membrane and the second membrane,
wherein the driver applies a magnetic force to the first membrane and the second membrane, causing the first membrane and the second membrane to deflect, and wherein such deflection of the first membrane and the second membrane results in a change of pressure within the first chamber, the second chamber, and the third chamber thereby resulting in fluid flow.

41. The micropump of claim 40 further comprising
a plurality of intermediate pump bodies disposed between the first pump body and the second pump body, wherein each intermediate pump body defines an intermediate fluid chamber including a side wall, an inlet, and an outlet, the inlet and outlet being in fluid communication with the intermediate fluid chamber; and
a plurality of intermediate flexible membranes, wherein each intermediate flexible membrane is disposed between adjacent intermediate pump bodies, and wherein the driver is magnetically coupled to each of the intermediate membranes.

* * * * *